(12) United States Patent
Pinner et al.

(10) Patent No.: US 9,416,166 B2
(45) Date of Patent: Aug. 16, 2016

(54) CD44 SPLICE VARIANTS IN NEURODEGENERATIVE DISEASES

(71) Applicant: NEURIM PHARAMCEUTICALS (1991) LTD., Tel Aviv (IL)

(72) Inventors: Elhanan Pinner, Beit Yitzhak (IL); Moshe Laudon, Kfar Saba (IL); Nava Zisapel, Tel Aviv (IL)

(73) Assignee: Neurim Pharmaceuticals (1991) Ltd., Tel Aviv (IL)

( * ) Notice: Subject to any disclaimer, the term of this patent is extended or adjusted under 35 U.S.C. 154(b) by 0 days.

(21) Appl. No.: 14/671,281

(22) Filed: Mar. 27, 2015

(65) Prior Publication Data

US 2015/0266940 A1    Sep. 24, 2015

Related U.S. Application Data

(62) Division of application No. 12/668,563, filed as application No. PCT/IB2008/052786 on Jul. 10, 2008, now Pat. No. 9,018,180.

(60) Provisional application No. 60/929,706, filed on Jul. 10, 2007.

(51) Int. Cl.
| | |
|---|---|
| *A61K 48/00* | (2006.01) |
| *C07K 14/705* | (2006.01) |
| *C12Q 1/68* | (2006.01) |
| *G01N 33/68* | (2006.01) |
| *C07K 16/28* | (2006.01) |

(52) U.S. Cl.
CPC ....... *C07K 14/70585* (2013.01); *C07K 16/2884* (2013.01); *C12Q 1/6883* (2013.01); *G01N 33/6896* (2013.01); *C07K 2317/76* (2013.01); *C12Q 2600/158* (2013.01); *G01N 2800/2814* (2013.01); *G01N 2800/2821* (2013.01); *G01N 2800/2835* (2013.01)

(58) Field of Classification Search
CPC .................................................... A61K 48/00
See application file for complete search history.

(56) References Cited

U.S. PATENT DOCUMENTS

| | | | |
|---|---|---|---|
| 5,990,299 | A | 11/1999 | Ruzdijic |
| 6,150,162 | A | 11/2000 | Bennett |
| 6,506,559 | B1 | 1/2003 | Fire |
| 2003/0143732 | A1 | 7/2003 | Fosnaugh |
| 2004/0259247 | A1 | 12/2004 | Tuschl |
| 2006/0199208 | A1 | 9/2006 | Srinivasan |
| 2006/0223065 | A1 | 10/2006 | Von Der Kammer |

FOREIGN PATENT DOCUMENTS

| | | |
|---|---|---|
| WO | 00/75312 | 12/2000 |
| WO | 01/75164 | 10/2001 |
| WO | 02/076510 | 10/2002 |
| WO | 02/097044 | 12/2002 |
| WO | 20061134128 | 12/2006 |

OTHER PUBLICATIONS

Bendall et al., (2004) Role of CD44 variant exon 6 in acute lymphoblastic leukaemia: association with altered bone marrow localisation and increased tumour burden. Leukemia 18(7): 1308-11.
Jackson et al., (1992) Multiple variants of the human lymphocyte homing receptor CD44 generated by insertions at a single site in the extracellular domain. J Biol Chem 267(7): 4732-9.
McKallip et al., (2003) Targeted deletion of CD44v7 exon leads to decreased endothelial cell injury but not tumor cell killing mediated by interleukin-2-activated cytolytic lymphocytes. J Biol Chem 278(44): 43818-30.
Akiyama et al., (1993) Morphological diversities of CD44 positive astrocytes in the cerebral cortex of normal subjects and patients with Alzheimer's disease. Brain Res 632(1-2): 249-259.
Aruffo et al., (1990) CD44 is the principal cell surface receptor for hyaluronate. Cell 61(7): 1303-1313.
Bell et al., (1998) Influence of intron length on alternative splicing of CD44. Mol Cell Biol 18(10): 5930-5941.
Boillee et al., (2006) ALS: a disease of motor neurons and their nonneuronal neighbors Neuron 52(1): 39-59.
Brummelkamp et al, (2002) A system for stable expression of short interfering RNAs in mammalian cells. Science 296: 550-553.
Caplen et al, (2001) Specific inhibition of gene expression by small double-stranded RNAs in invertebrate and vertebrate systems. Proc Natl Acad Sci USA 98(17): 9742-9747.
Cheng et al., (2006) A positive feedback loop couples Ras activation and CD44 alternative splicing. Genes Dev 20: 1715-1720.
Di Giorgio et al., (2007) Non-cell autonomous effect of glia on motor neurons in an embryonic 15 stem cell-based ALS model Nat Neurosci 10(5): 608-614.
Dimitroff et al., (2000) A distinct glycoform of CD44 is an L-selectin ligand on human hematopoietic cells. PNAS 97: 13841-13846.

(Continued)

*Primary Examiner* — Kimberly Chong
(74) *Attorney, Agent, or Firm* — Rodney J. Fuller; Booth Udall Fuller, PLC

(57) ABSTRACT

There is provided a method of treating or preventing a neurodegenerative disease, which includes administration of a composition that includes a reagent capable of modulating expression of ribonucleic acid (RNA) encoded by a nucleic acid, wherein the nucleic acid is selected from a group that includes a contiguous nucleotide sequence being at least 90% homologous to at least 20 nucleotides of: SEQ ID NO: 1, SEQ ID NO: 3, SEQ ID NO: 5, SEQ ID NO: 7, or any combination thereof. There is further provided a method of treating or preventing a neurodegenerative disease, which includes administration of a composition that includes a reagent capable of modulating expression and/or activity of a polypeptide, wherein the sequence of the polypeptide is selected from a group that includes a contiguous amino acid sequence being at least 90% homologous to at least 10 amino acid of: SEQ ID NO: 2, SEQ ID NO: 4, SEQ ID NO: 6, SEQ ID NO: 8, or any combination thereof.

17 Claims, 5 Drawing Sheets

(56) References Cited

OTHER PUBLICATIONS

Dimitroff et al., (2001) CD44 is a major E-selectin ligand on human hematopoietic progenitor cells J Cell Biol 153(6): 1277-1286.

Du et al., (2007) Correction of prototypic ATM splicing mutations and aberrant ATM function with antisense morpholino oligonucleotides. Proc Natl Acad Sci USA 104: 6007-6012.

Elbashir et al, (2001) Duplexes of 21-nucleotide RNAs mediate RNA interference in cultured mammalian cells. Nature 411: 494-498.

Elbashir et al, (2001) Functional anatomy of siRNAs for mediating efficient RNAi in Drosophila melanogaster embryo lysate. EMBO J 20(23): 6877-6888.

Elbashir et al, (2001) RNA interference is mediated by 21- and 22-nucleotide RNAs Genes Dev 15(2): 188-200.

Esposito et al., (2007) Non-steroidal anti-inflammatory drugs in Parkinson's disease. Exp Neurol 205(2): 295-312.

Faassen et al., (1992) A cell surface chondroitin sulfate proteoglycan, immunologically related to CD44, is involved in type I collagen-mediated melanoma cell motility and invasion. J Cell Biol 116(2): 521-531.

Fujimoto et al., (2001) CD44 binds a chondroitin sulfate proteoglycan, aggrecan. Int Immunol 13(3): 359-366.

Garin et al., (2007) CD44 variant DNA vaccination with virtual lymph node ameliorates experimental autoimmune encephalomyelitis through the induction of apoptosis. J Neurol Sci 258(1-2): 17-26.

Gunthert (1993) CD44: a multitude of isoforms with diverse functions. Curr Top Microbiol Immunol 184: 47-63.

Gunthert et al., (1991) A new variant of glycoprotein CD44 confers metastatic potential to rat carcinoma cells. Cell 65 (1): 13-24.

Guriec et al., (1997) CD44 isoforms with exon v6 and metastasis of primary NOMO breast carcinomas. Breast Cancer Res Treat 44(3): 261-268.

Haegel et al., (1993) Activated mouse astrocytes and T cells express similar CD44 variants. Role 40 of CD44 in astrocyte/T cell binding J Cell Biol 122(5): 1067-1077.

Haynes et al, (1991) Measurement of an adhesion molecule as an indicator of inflammatory disease activity. Up-regulation of the receptor for hyaluronate (CD44) in rheumatoid arthritis. Arthritis Rheum 34(11): 1434-1443.

Heider et al., (1993) A human homologue of the rat metastasis-associated variant of CD44 is expressed in colorectal carcinomas and adenomatous polyps. J Cell Biol 120(1): 227-233.

Herrlich et al., (1993) CD44 splice variants: metastases meet lymphocytes. Immunol Today 14(8): 395-9.

Hua et al, (2007) Enhancement of SMN2 exon 7 inclusion by antisense oligonucleotides targeting the exon. PLoS Biol 5: e73.

Jalkanen et al., (1992) Lymphocyte CD44 binds the COOH-terminal heparin-binding domain of fibronectin. J Cell Biol 116(3): 817-825.

Kim and Joh (2006) Microglia, major player in the brain inflammation: their roles in the pathogenesis of Parkinson's disease. Exp Mol Med 38(4): 333-347.

Laman et al., (1998) Therapy with antibodies against CD40L (CD154) and CD44-variant isoforms reduces experimental autoimmune encephalomyelitis induced by a proteolipid protein peptide Mult Scler 4(3): 147-153.

Lesley et al., (1995) Site-specific de-N-glycosylation of CD44 can activate hyaluronan binding, and CD44 activation states show distinct threshold densities for hyaluronan binding. J Exp Med 182(2): 431-437.

Lobsiger et al., (2007) Toxicity from different SOD1 mutants dysregulates the complement system and the neuronal regenerative response in ALS motor neurons. Proc Natl Acad USA Sci 104(18): 7319-7326.

Matsuoka et al., (2000) CD44 splice variant involvement in the chronic inflammatory disease of the spinal cord: HAM/TSP. J Neuroimmunol 102(1): 1-7.

McKallip et al., (2005) Role of CD44 and its v7 isoform in staphylococcal enterotoxin B-induced toxic shock: CD44 deficiency on hepatic mononuclear cells leads to reduced activation-induced apoptosis that results in increased liver damage. Infect Immun 73(1): 50-61.

Meade and Dowdy (2007) Exogenous siRNA delivery using peptide transduction domains/cell penetrating peptides. Adv Drug Deliv Rev 59: 134-140.

Merrifield (1964) Solid-phase peptide synthesis. 3. An improved synthesis of bradykinin. Biochemistry 3(9): 1385-1390.

Miyake et al., (1990) Hyaluronate can function as a cell adhesion molecule and CD44 participates in hyaluronate recognition. J Exp Med 172(1): 69-75.

Naor et al., (2002) CD44 in cancer. Crit Rev Clin Lab Sci 39(6): 527-579.

Hong-Min et al., (2002) Expression of CD44 variants in colorectal carcinoma quantified by real-time reverse transcriptase-polymerase chain reaction. J Lab Clin Med 139(1): 59-65.

Peach et al., (1993) Identification of hyaluronic acid binding sites in the extracellular domain of CD44. J Cell Biol 122 (1): 257-264.

Pehar et al., (2005) Complexity of astrocyte-motor neuron interactions in amyotrophic lateral sclerosis Neurodegener. Dis 2(3-4): 139-146.

Pickford et al, (2008) The autophagy-related protein beclin 1 shows reduced expression in early Alzheimer disease and regulates amyloid beta accumulation in mice. J Clin Invest 118(6): 2190-2199.

Ravikumar et al., (2004) Inhibition of mTOR induces autophagy and reduces toxicity of polyglutamine expansions in fly and mouse models of Huntington disease. Nat Genet 36(6): 585-595.

Reber et al, (1990) Retardation of metastatic tumor growth after immunization with metastasisspecific monoclonal antibodies. Int J Cancer 46(5): 919-927.

Ristamaki et al., (1994) Serum CD44 in malignant lymphoma: an association with treatment response. Blood 84(1): 238-243.

Rothman et al, (1991) Human T cell activation by OKT3 is inhibited by a monoclonal antibody to CD44. J Immunol 147 (8): 2493-2499.

Screaton et al., (1992) Genomic structure of DNA encoding the lymphocyte homing receptor CD44 reveals at least 12 alternatively spliced exons. PNAS 89: 12160-12164.

Screaton et al., (1993) The identification of a new alternative exon with highly restricted tissue expression in transcripts encoding the mouse Pgp-1 (CD44) homing receptor. Comparison of all 10 variable exons between mouse, human, and rat. J Biol Chem 268(17): 12235-12238.

Shibata et al., (2006) Regulation of intracellular accumulation of mutant Huntingtin by Beclin 1. J Biol Chem 281(20): 14474-14485.

Singleton et al., (2006) Transaction of Sphingosine 1-phosphate receptor is essential for vascular barrier regulation J Biol Chem 281(45): 34381-34393.

Stamenkovic et al., (1991) The hematopoietic and epithelial forms of CD44 are distinct polypeptides with different adhesion potentials for hyaluronate-bearing cells. Embo J 1991 10(2): 343-348.

Suzuki et al., (1996) Differential expression of CD44 variants among meningioma subtypes Clin Mol Pathol 49(3): M140-M146.

Tolg al, (1993) Splicing choice from ten variant exons establishes CD44 variability NAR 21(5): 1225-1229.

Tsukita et al., (1994) ERM family members as molecular linkers between the cell surface glycoprotein CD44 and actin-based cytoskeletons. J Cell Biol 126(2): 391-401.

Tuschl and Borkhardt (2002) Small interfering RNAs: a revolutionary tool for the analysis of gene function and gene therapy. Molecular Intervent 2(3): 158-167.

Van der Voort, et al, (1995) Binding of cell-surface expressed CD44 to hyaluronate is dependent on splicing and cell type. Biochem Biophys Res Commun 214: 135-144.

Vogel et al., (1992) H-CAM expression in the human nervous system: evidence for a role in diverse glial interactions. J Neurocytol 21(5): 363-73.

Weg-Remers et al., (2001) Regulation of alternative pre-mRNA splicing by the ERK MAP-kinase pathway. EMBO J 20 (15): 4194-4203.

(56) References Cited

OTHER PUBLICATIONS

Wielenga et al., (1993) Expression of CD44 variant proteins in human colorectal cancer is related to tumor progression. Cancer Res 53(20): 4754-4756.

Yu et al., (2005) Macroautophagy—a novel Beta-amyloid peptide-generating pathway activated in Alzheimer's disease. J Cell Biol 171(1): 87-98.

Database entry GSN:AAD54979; cited in corresponding EP 2167692 examination Oct. 21, 2011.

Database entry GSN:AAD48132; cited in corresponding EP 2167692 examination Oct. 21, 2011.

Database entry GSP:AAE36362; cited in corresponding EP 2167692 examination Oct. 21, 2011.

Database entry UNIPROT:Q62913; cited in corresponding EP 2167692 examination Oct. 21, 2011.

Fig. 2:

A.
GTACGTCTTCAAATACCATCTCAGCAGGCTGGGAGCCAAATGAAGAAAATGAAGATGAAAGAGA
  T  S  S  N  T  I  S  A  G  W  E  P  N  E  E  N  E  D  E  R  D
CAGACACCTCAGTTTTCTGGATCAGGCATTGATGATGATGAAGATTTTATCTCCAGCACCA
  R  H  L  S  F  S  G  S  G  I  D  D  D  E  D  F  I  S  S  T

B.
      Exon C5                              Exon V3
GACAGCACAGACAGAATCCCTGCTACCA ⌐       ⌐ GTACGTCTTCAAATACCATCTCAGCAGGC
 D  S  T  D  R  I  P  A  T  S           T  S  S  N  T  I  S  A  G C.
      Exon V3                              Exon C6
GATGATGAAGATTTTATCTCCAGCACCA ⌐       ⌐ GAGACCAAGACACATTCCACCCCAGTGGG
 D  D  E  D  F  I  S  S  T  R           D  Q  D  T  F  H  P  S  G

Fig. 3:

A.
TCCAGGCAACTCCTAGTAGTACAACGGAAGAAACAGCTACCCAGAAGGAACAGTGGTTTGGCAA
   Q  A  T  P  S  S  T  T  E  E  T  A  T  Q  K  E  Q  W  F  G  N
CAGATGGCATGAGGGATATCGCCAAACACCCAAAGAAGACTCCCATTCGACAACAGGGACAGCT
  R  W  H  E  G  Y  R  Q  T  P  K  E  D  S  H  S  T  T  G  T  A

B.
      Exon C5                              Exon V6
GACAGCACAGACAGAATCCCTGCTACCA ⌐       ⌐ TCCAGGCAACTCCTAGTAGTACAACGGAA
 D  S  T  D  R  I  P  A  T  I           Q  A  T  P  S  S  T  T  E C.
      Exon V6                              Exon C6
GACTCCCATTCGACAACAGGGACAGCTG ⌐       ⌐ GAGACCAAGACACATTCCACCCCAGTGGG
 D  S  H  S  T  T  G  T  A  G           D  Q  D  T  F  H  P  S  G

Fig. 4

A.
CAGCCTCAGCTCATACCAGCCATCCAATGCAAGGAAGGACAACACCAAGCCCAGAG
  A  S  A  H  T  S  H  P  M  Q  G  R  T  T  P  S  P  E
GACAGTTCCTGGACTGATTTCTTCAACCCAATCTCACACCCCATGGGACGAGGTCA
 D  S  S  W  T  D  F  F  N  P  I  S  H  P  M  G  R  G  H
TCAAGCAGGAAGAAGGATGG
  Q  A  G  R  R  M

B.
     Exon C5                              Exon V7
GACAGCACAGACAGAATCCCTGCTACCA      CAGCCTCAGCTCATACCAGCCATCCAATG
 D  S  T  D  R  I  P  A  T  T       A  S  A  H  T  S  H  P  M C.
     Exon V7                              Exon C6
CGAGGTCATCAAGCAGGAAGAAGGATGG      GAGACCAAGACACATTCCACCCCAGTGGG
 R  G  H  Q  A  G  R  R  M  G       D  Q  D  T  F  H  P  S  G

Fig. 5:

A.
ATAGGAATGATGTCACAGGTGGAAGAAGAGACCCAAATCATTCTGAAGGCTCAACTACTTTACT
  R  N  D  V  T  G  G  R  R  D  P  N  H  S  E  G  S  T  T  L  L
GGAAGGTTATACCTCTCATTACCCACACACGAAGGAAAGCAGGACCTTCATCCCAGTGACCTCA
  E  G  Y  T  S  H  Y  P  H  T  K  E  S  R  T  F  I  P  V  T  S
GCTAAGACTGGGTCCTTTGGAGTTACTGCAGTTACTGTTGGAGATTCCAACTCTAATGTCAATC
  A  K  T  G  S  F  G  V  T  A  V  T  V  G  D  S  N  S  N  V  N  R
GTTCCTTATCAG
  S  L  S

B.
     Exon C5                              Exon V10
GACAGCACAGACAGAATCCCTGCTACCA      ATAGGAATGATGTCACAGGTGGAAGAAGA
 D  S  T  D  R  I  P  A  T  N       R  N  D  V  T  G  G  R  R C.
     Exon V10                             Exon C6
AACTCTAATGTCAATCGTTCCTTATCAG      GAGACCAAGACACATTCCACCCCAGTGGG
 N  S  N  V  N  R  S  L  S  G       D  Q  D  T  F  H  P  S  G

SEQUENCE LISTING

<160> NUMBER OF SEQ ID NOS: 8

<210> SEQ ID NO 1
<211> LENGTH: 1212
<212> TYPE: DNA
<213> ORGANISM: Homo sapiens

<400> SEQUENCE: 1

```
atggacaagt tttggtggca cgcagcctgg ggactctgcc tcgtgccgct gagcctggcg      60
cagatcgatt tgaatataac ctgccgcttt gcaggtgtat tccacgtgga gaaaaatggt     120
cgctacagca tctctcggac ggaggccgct gacctctgca aggctttcaa tagcaccttg     180
```

```
cccacaatgg cccagatgga gaaagctctg agcatcggat ttgagacctg caggtatggg    240
ttcatagaag ggcacgtggt gattccccgg atccacccca actccatctg tgcagcaaac    300
aacacagggg tgtacatcct cacatccaac acctcccagt atgacacata ttgcttcaat    360
gcttcagctc cacctgaaga agattgtaca tcagtcacag acctgcccaa tgcctttgat    420
ggaccaatta ccataactat tgttaaccgt gatggcaccc gctatgtcca gaaggagaa    480 tacagaacga atcctgaaga catctacccc agcaaccctä ctgatgatga cgtgagcagc    540
ggctcctcca gtgaaaggag cagcacttca ggaggttaca tcttttacac ctttctact    600 gtacacccca tcccagacga agacagtccc tggatcaccg acagcacaga cagaatccct    660
gctaccagta cgtcttcaaa taccatctca gcaggctggg agccaaatga agaaaatgaa    720
gatgaaagag acagacacct cagttttct ggatcaggca ttgatgatga tgaagatttt    780
atctccagca ccagagacca agacacattc caccccagtg ggggtccca taccactcat    840 ggatctgaat cagatggaca ctcacatggg agtcaagaag gtggagcaaa cacaacctct    900
ggtcctataa ggacacccca aattccagaa tggctgatca tcttggcatc cctcttggcc    960
ttggctttga ttcttgcagt ttgcattgca gtcaacagtc gaagaaggtg tgggcagaag    1020
aaaaagctag tgatcaacag tggcaatgga gctgtggagg acagaaagcc aagtggactc    1080
aacggagagg ccagcaagtc tcaggaaatg gtgcatttgg tgaacaagga gtcgtcagaa    1140
actccagacc agtttatgac agctgatgag acaaggaacc tgcagaatgt ggacatgaag    1200
attggggtgt aa                                                       1212
```

<210> SEQ ID NO 2
<211> LENGTH: 403
<212> TYPE: PRT
<213> ORGANISM: Homo sapiens

<400> SEQUENCE: 2

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
```

|     |     |     | 180 |     |     |     | 185 |     |     |     | 190 |     |     |
| --- | --- | --- | --- | --- | --- | --- | --- | --- | --- | --- | --- | --- | --- |
| Tyr | Ile | Phe | Tyr | Thr | Phe | Ser | Thr | Val | His | Pro | Ile | Pro | Asp | Glu | Asp |
|     |     |     |     | 195 |     |     |     | 200 |     |     |     | 205 |     |     |     |
| Ser | Pro | Trp | Ile | Thr | Asp | Ser | Thr | Asp | Arg | Ile | Pro | Ala | Thr | Ser | Thr |
|     | 210 |     |     |     | 215 |     |     |     | 220 |     |     |     |     |     |     |
| Ser | Ser | Asn | Thr | Ile | Ser | Ala | Gly | Trp | Glu | Pro | Asn | Glu | Glu | Asn | Glu |
| 225 |     |     |     |     | 230 |     |     |     |     | 235 |     |     |     |     | 240 |
| Asp | Glu | Arg | Asp | Arg | His | Leu | Ser | Phe | Ser | Gly | Ser | Gly | Ile | Asp | Asp |
|     |     |     |     | 245 |     |     |     |     | 250 |     |     |     |     | 255 |     |
| Asp | Glu | Asp | Phe | Ile | Ser | Ser | Thr | Arg | Asp | Gln | Asp | Thr | Phe | His | Pro |
|     |     |     | 260 |     |     |     |     | 265 |     |     |     |     | 270 |     |     |
| Ser | Gly | Gly | Ser | His | Thr | Thr | His | Gly | Ser | Glu | Ser | Asp | Gly | His | Ser |
|     |     | 275 |     |     |     |     | 280 |     |     |     |     | 285 |     |     |     |
| His | Gly | Ser | Gln | Glu | Gly | Gly | Ala | Asn | Thr | Thr | Ser | Gly | Pro | Ile | Arg |
|     |     | 290 |     |     |     |     | 295 |     |     |     |     | 300 |     |     |     |
| Thr | Pro | Gln | Ile | Pro | Glu | Trp | Leu | Ile | Ile | Leu | Ala | Ser | Leu | Leu | Ala |
| 305 |     |     |     |     | 310 |     |     |     |     | 315 |     |     |     |     | 320 |
| Leu | Ala | Leu | Ile | Leu | Ala | Val | Cys | Ile | Ala | Val | Asn | Ser | Arg | Arg | Arg |
|     |     |     |     | 325 |     |     |     |     | 330 |     |     |     |     | 335 |     |
| Cys | Gly | Gln | Lys | Lys | Leu | Val | Ile | Asn | Ser | Gly | Asn | Gly | Ala | Val |
|     |     |     | 340 |     |     |     |     | 345 |     |     |     |     | 350 |     |
| Glu | Asp | Arg | Lys | Pro | Ser | Gly | Leu | Asn | Gly | Glu | Ala | Ser | Lys | Ser | Gln |
|     | 355 |     |     |     |     | 360 |     |     |     |     | 365 |     |     |     |     |
| Glu | Met | Val | His | Leu | Val | Asn | Lys | Glu | Ser | Ser | Glu | Thr | Pro | Asp | Gln |
|     | 370 |     |     |     |     | 375 |     |     |     |     | 380 |     |     |     |     |
| Phe | Met | Thr | Ala | Asp | Glu | Thr | Arg | Asn | Leu | Gln | Asn | Val | Asp | Met | Lys |
| 385 |     |     |     |     | 390 |     |     |     |     | 395 |     |     |     |     | 400 |
| Ile | Gly | Val |

<210> SEQ ID NO 3
<211> LENGTH: 1215
<212> TYPE: DNA
<213> ORGANISM: Homo sapiens

<400> SEQUENCE: 3

```
atggacaagt tttggtggca cgcagcctgg ggactctgcc tcgtgccgct gagcctggcg      60
cagatcgatt tgaatataac ctgccgcttt gcaggtgtat tccacgtgga gaaaaatggt     120
cgctacagca tctctcggac ggaggccgct gacctctgca aggctttcaa tagcaccttg     180
cccacaatgg cccagatgga gaaagctctg agcatcggat tgagacctgc aggtatgggg     240
ttcatagaag ggcacgtggt gattccccgg atccacccca actccatctg tgcagcaaac     300
aacacagggg tgtacatcct cacatccaac acctcccagt atgacacata ttgcttcaat     360
gcttcagctc acctgaaga agattgtaca tcagtcacag acctgcccaa tgcctttgat     420
ggaccaatta ccataactat tgttaaccgt gatggcaccc gctatgtcca gaaggagaa     480
tacagaacga atcctgaaga catctacccc agcaaccta ctgatgatga cgtgagcagc     540
ggctcctcca gtgaaaggag cagcacttca ggaggttaca tcttttacac cttttctact     600
gtacacccca tccagacga agacagtccc tggatcaccg acagcacaga cagaatccct     660
gctaccatcc aggcaactcc tagtagtaca acggaagaaa cagctaccca gaaggaacag     720
tggtttggca acagatggca tgagggatat cgccaaacac ccagagaaga ctcccattcg     780
acaacaggga cagctggaga ccaagacaca ttccaccccca gtgggggggtc ccataccact     840
```

```
catggatctg aatcagatgg acactcacat gggagtcaag aaggtggagc aaacacaacc      900
tctggtccta taaggacacc ccaaattcca gaatggctga tcatcttggc atccctcttg      960
gccttggctt tgattcttgc agtttgcatt gcagtcaaca gtcgaagaag gtgtgggcag     1020
aagaaaaagc tagtgatcaa cagtggcaat ggagctgtgg aggacagaaa gccaagtgga     1080
ctcaacggag aggccagcaa gtctcaggaa atggtgcatt tggtgaacaa ggagtcgtca     1140
gaaactccag accagtttat gacagctgat gagacaagga acctgcagaa tgtggacatg     1200
aagattgggg tgtaa                                                      1215
```

<210> SEQ ID NO 4
<211> LENGTH: 404
<212> TYPE: PRT
<213> ORGANISM: Homo sapiens

<400> SEQUENCE: 4

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Ile Gln
    210                 215                 220

Ala Thr Pro Ser Ser Thr Thr Glu Glu Thr Ala Thr Gln Lys Glu Gln
225                 230                 235                 240

Trp Phe Gly Asn Arg Trp His Glu Gly Tyr Arg Gln Thr Pro Arg Glu
                245                 250                 255

Asp Ser His Ser Thr Thr Gly Thr Ala Gly Asp Gln Asp Thr Phe His
            260                 265                 270

Pro Ser Gly Gly Ser His Thr Thr His Gly Ser Glu Ser Asp Gly His
        275                 280                 285

Ser His Gly Ser Gln Glu Gly Gly Ala Asn Thr Thr Ser Gly Pro Ile
    290                 295                 300
```

```
Arg Thr Pro Gln Ile Pro Glu Trp Leu Ile Ile Leu Ala Ser Leu Leu
305                 310                 315                 320

Ala Leu Ala Leu Ile Leu Ala Val Cys Ile Ala Val Asn Ser Arg Arg
            325                 330                 335

Arg Cys Gly Gln Lys Lys Leu Val Ile Asn Ser Gly Asn Gly Ala
        340                 345                 350

Val Glu Asp Arg Lys Pro Ser Gly Leu Asn Gly Glu Ala Ser Lys Ser
            355                 360                 365

Gln Glu Met Val His Leu Val Asn Lys Glu Ser Ser Glu Thr Pro Asp
    370                 375                 380

Gln Phe Met Thr Ala Asp Glu Thr Arg Asn Leu Gln Asn Val Asp Met
385                 390                 395                 400

Lys Ile Gly Val

<210> SEQ ID NO 5
<211> LENGTH: 1218
<212> TYPE: DNA
<213> ORGANISM: Homo sapiens

<400> SEQUENCE: 5
atggacaagt tttggtggca cgcagcctgg ggactctgcc tcgtgccgct gagcctggcg    60
cagatcgatt tgaatataac ctgccgcttt gcaggtgtat tccacgtgga gaaaaatggt   120
cgctacagca tctctcggac ggaggccgct gacctctgca aggctttcaa tagcaccttg   180
cccacaatgg cccagatgga gaaagctctg agcatcggat ttgagacctg caggtatggg   240
ttcatagaag ggcacgtggt gattccccgg atccacccca actccatctg tgcagcaaac   300
aacacagggg tgtacatcct cacatccaac acctcccagt atgacacata ttgcttcaat   360
gcttcagctc cacctgaaga agattgtaca tcagtcacag acctgcccaa tgcctttgat   420
ggaccaatta ccataactat tgttaaccgt gatggcaccc gctatgtcca gaaaggagaa   480
tacagaacga atcctgaaga catctacccc agcaaccctg ctgatgatga cgtgagcagc   540
ggctcctcca gtgaaaggag cagcacttca ggaggttaca tcttttacac cttttctact   600
gtacacccca tcccagacga agacagtccc tggatcaccg acagcacaga cagaatccct   660
gctaccacag cctcagctca taccagccat ccaatgcaag gaaggacaac accaagccca   720
gaggacagtt cctggactga tttcttcaac ccaatctcac ccccatgggg acgaggtcat   780
caagcaggaa gaaggatggg agaccaagac acattccacc ccagtggggg gtcccatacc   840
actcatggat ctgaatcaga tggacactca catgggagtc aagaaggtgg agcaaacaca   900
acctctggtc ctataaggac accccaaatt ccagaatggc tgatcatctt ggcatccctc   960
ttggccttgg ctttgattct tgcagtttgc attgcagtca cagtcgaag aaggtgtggg  1020 cagaagaaaa agctagtgat caacagtggc aatggagctg tggaggacag aaagccaagt  1080
ggactcaacg gagaggccag caagtctcag gaaatggtgc atttggtgaa caaggagtcg  1140
tcagaaactc cagaccagtt tatgacagct gatgagacag gaacctgca gaatgtggac  1200 atgaagattg gggtgtaa                                                 1218

<210> SEQ ID NO 6
<211> LENGTH: 405
<212> TYPE: PRT
<213> ORGANISM: Homo sapiens

<400> SEQUENCE: 6

Met Asp Lys Phe Trp Trp His Ala Ala Trp Gly Leu Cys Leu Val Pro
```

```
            1               5                  10                 15
        Leu Ser Leu Ala Gln Ile Asp Leu Asn Ile Thr Cys Arg Phe Ala Gly
                        20                  25                 30

Val Phe His Val Glu Lys Asn Gly Arg Tyr Ser Ile Ser Arg Thr Glu
                        35                  40                 45

Ala Ala Asp Leu Cys Lys Ala Phe Asn Ser Thr Leu Pro Thr Met Ala
                        50                  55                 60

Gln Met Glu Lys Ala Leu Ser Ile Gly Phe Glu Thr Cys Arg Tyr Gly
         65                  70                  75                 80

Phe Ile Glu Gly His Val Val Ile Pro Arg Ile His Pro Asn Ser Ile
                             85                  90                 95

Cys Ala Ala Asn Asn Thr Gly Val Tyr Ile Leu Thr Ser Asn Thr Ser
                            100                 105                110

Gln Tyr Asp Thr Tyr Cys Phe Asn Ala Ser Ala Pro Pro Glu Glu Asp
                            115                 120                125

Cys Thr Ser Val Thr Asp Leu Pro Asn Ala Phe Asp Gly Pro Ile Thr
                            130                 135                140

Ile Thr Ile Val Asn Arg Asp Gly Thr Arg Tyr Val Gln Lys Gly Glu
        145                 150                 155                160

Tyr Arg Thr Asn Pro Glu Asp Ile Tyr Pro Ser Asn Pro Thr Asp Asp
                            165                 170                175

Asp Val Ser Ser Gly Ser Ser Ser Glu Arg Ser Ser Ser Ser Gly Gly
                            180                 185                190

Tyr Ile Phe Tyr Thr Phe Ser Thr Val His Pro Ile Pro Asp Glu Asp
                            195                 200                205

Ser Pro Trp Ile Thr Asp Ser Thr Asp Arg Ile Pro Ala Thr Thr Ala
                            210                 215                220

Ser Ala His Thr Ser His Pro Met Gln Gly Arg Thr Thr Pro Ser Pro
        225                 230                 235                240

Glu Asp Ser Ser Trp Thr Asp Phe Phe Asn Pro Ile Ser His Pro Met
                            245                 250                255

Gly Arg Gly His Gln Ala Gly Arg Arg Met Gly Asp Gln Asp Thr Phe
                            260                 265                270

His Pro Ser Gly Gly Ser His Thr Thr His Gly Ser Glu Ser Asp Gly
                            275                 280                285

His Ser His Gly Ser Gln Glu Gly Gly Ala Asn Thr Thr Ser Gly Pro
                            290                 295                300

Ile Arg Thr Pro Gln Ile Pro Glu Trp Leu Ile Ile Leu Ala Ser Leu
        305                 310                 315                320

Leu Ala Leu Ala Leu Ile Leu Ala Val Cys Ile Ala Val Asn Ser Arg
                            325                 330                335

Arg Arg Cys Gly Gln Lys Lys Lys Leu Val Ile Asn Ser Gly Asn Gly
                            340                 345                350

Ala Val Glu Asp Arg Lys Pro Ser Gly Leu Asn Gly Glu Ala Ser Lys
                            355                 360                365

Ser Gln Glu Met Val His Leu Val Asn Lys Glu Ser Ser Glu Thr Pro
        370                 375                 380

Asp Gln Phe Met Thr Ala Asp Glu Thr Arg Asn Leu Gln Asn Val Asp
        385                 390                 395                400

Met Lys Ile Gly Val
                            405

<210> SEQ ID NO 7
```

<211> LENGTH: 1290
<212> TYPE: DNA
<213> ORGANISM: Homo sapiens

<400> SEQUENCE: 7

```
atggacaagt tttggtggca cgcagcctgg ggactctgcc tcgtgccgct gagcctggcg      60
cagatcgatt tgaatataac ctgccgcttt gcaggtgtat tccacgtgga gaaaaatggt     120
cgctacagca tctctcggac ggaggccgct gacctctgca aggctttcaa tagcaccttg     180
cccacaatgg cccagatgga gaaagctctg agcatcggat ttgagacctg caggtatggg     240
ttcatagaag gcacgtggt gattcccgg atccacccca actccatctg tgcagcaaac      300
aacacagggg tgtacatcct cacatccaac acctcccagt atgacacata ttgcttcaat     360
gcttcagctc cacctgaaga agattgtaca tcagtcacag acctgcccaa tgcctttgat     420
ggaccaatta ccataactat tgttaaccgt gatggcaccc gctatgtcca gaaggagaa      480
tacagaacga atcctgaaga catctacccc agcaaccta ctgatgatga cgtgagcagc      540
ggctcctcca gtgaaaggag cagcacttca ggaggttaca tcttttacac ctttctact      600
gtacacccca tcccagacga agacagtccc tggatcaccg acagcacaga cagaatccct     660
gctaccaata ggaatgatgt cacaggtgga agaagagacc caaatcattc tgaaggctca     720
actactttac tggaaggtta tacctctcat tacccacaca cgaaggaaag caggaccttc     780
atcccagtga cctcagctaa gactgggtcc tttggagtta ctgcagttac tgttggagat     840
tccaactcta atgtcaatcg ttccttatca ggagaccaag acacattcca ccccagtggg     900
gggtcccata ccactcatgg atctgaatca gatggacact cacatgggag tcaagaaggt     960
ggagcaaaca aacctctgg tcctataagg acaccccaaa ttccagaatg ctgatcatc     1020
ttggcatccc tcttggcctt ggctttgatt cttgcagttt gcattgcagt caacagtcga    1080
agaaggtgtg ggcagaagaa aaagctagtg atcaacagtg gcaatggagc tgtggaggac    1140
agaaagccaa gtggactcaa cggagaggcc agcaagtctc aggaaatggt gcatttggtg    1200
aacaaggagt cgtcagaaac tccagaccag tttatgacag ctgatgagac aaggaacctg    1260
cagaatgtgg acatgaagat tggggtgtaa                                     1290
```

<210> SEQ ID NO 8
<211> LENGTH: 429
<212> TYPE: PRT
<213> ORGANISM: Homo sapiens

<400> SEQUENCE: 8

```
Met Asp Lys Phe Trp Trp His Ala Ala Trp Gly Leu Cys Leu Val Pro
  1               5                  10                  15

Leu Ser Leu Ala Gln Ile Asp Leu Asn Ile Thr Cys Arg Phe Ala Gly
             20                  25                  30

Val Phe His Val Glu Lys Asn Gly Arg Tyr Ser Ile Ser Arg Thr Glu
         35                  40                  45

Ala Ala Asp Leu Cys Lys Ala Phe Asn Ser Thr Leu Pro Thr Met Ala
     50                  55                  60

Gln Met Glu Lys Ala Leu Ser Ile Gly Phe Glu Thr Cys Arg Tyr Gly
 65                  70                  75                  80

Phe Ile Glu Gly His Val Val Ile Pro Arg Ile His Pro Asn Ser Ile
                 85                  90                  95

Cys Ala Ala Asn Asn Thr Gly Val Tyr Ile Leu Thr Ser Asn Thr Ser
            100                 105                 110
```

-continued

```
Gln Tyr Asp Thr Tyr Cys Phe Asn Ala Ser Ala Pro Pro Glu Glu Asp
            115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
            195                 200                 205

Ser Pro Trp Ile Thr Asp Ser Thr Asp Arg Ile Pro Ala Thr Asn Arg
    210                 215                 220

Asn Asp Val Thr Gly Gly Arg Arg Asp Pro Asn His Ser Glu Gly Ser
225                 230                 235                 240

Thr Thr Leu Leu Glu Gly Tyr Thr Ser His Tyr Pro Thr His Thr Lys Glu
                245                 250                 255

Ser Arg Thr Phe Ile Pro Val Thr Ser Ala Lys Thr Gly Ser Phe Gly
                260                 265                 270

Val Thr Ala Val Thr Val Gly Asp Ser Asn Ser Asn Val Asn Arg Ser
            275                 280                 285

Leu Ser Gly Asp Gln Asp Thr Phe His Pro Ser Gly Gly Ser His Thr
    290                 295                 300

His Thr Gly Ser Glu Ser Asp Gly His Ser His Gly Ser Gln Glu Gly Gly
305                 310                 315                 320

Gly Ala Asn Thr Thr Ser Gly Pro Ile Arg Thr Pro Gln Ile Pro Glu
                325                 330                 335

Trp Leu Ile Ile Leu Ala Ser Leu Leu Ala Leu Ala Leu Ile Leu Ala
            340                 345                 350

Val Cys Ile Ala Val Asn Ser Arg Arg Arg Cys Gly Gln Lys Lys Lys
            355                 360                 365

Leu Val Ile Asn Ser Gly Asn Gly Ala Val Glu Asp Arg Lys Pro Ser
    370                 375                 380

Gly Leu Asn Gly Glu Ala Ser Lys Ser Gln Glu Met Val His Leu Val
385                 390                 395                 400

Asn Lys Glu Ser Ser Glu Thr Pro Asp Gln Phe Met Thr Ala Asp Glu
                405                 410                 415

Thr Arg Asn Leu Gln Asn Val Asp Met Lys Ile Gly Val
            420                 425
```

CD44 SPLICE VARIANTS IN NEURODEGENERATIVE DISEASES

RELATED APPLICATIONS

The present application is a divisional of U.S. patent application Ser. No. 12/668,563, filed Jan. 11, 2010 (published as U.S. Publication No. 20110172286), which is the U.S. National Stage of International Application No. PCT/IB2008/052786 filed Jul. 10, 2008, which claims the benefit of U.S. Provisional Application No. 60/929,706 filed Jul. 10, 2007, the contents of each of which are herein incorporated by reference in their entireties for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 21,114 byte ASCII (text) file named "Seq_List" created on Mar. 26, 2015.

BACKGROUND

CD44 is a Type I transmembrane glycoprotein expressed by virtually every cell in the vertebrate body. CD44 is a cell surface adhesion molecule, which has been shown to be involved in various processes, such as in cell trafficking, cell migration, cell homing, cell-cell interactions and cell-matrix interactions. The N-terminus of CD44 includes the extracellular ligand-binding domain of the molecule. Various ligands are known to interact with CD44. Hyaluronic acid (HA) is the principal ligand of CD44 (Miyake et al., J Exp Med 1990, 172:69-75, Aruffo et. al., Cell 1990, 61: 1303-13, Peach et. al., J Cell Biol 1993, 122:257-64), however, additional extracellular matrix (ECM) components (such as laminin, collagen, fibronectin and chondroitin sulfate (Jalkanen et. al., J Cell Biol 1992, 116:817-25, Faassen et. al., J Cell Biol 1992, 116:521-31) as well as non-ECM constituents (mucosal vascular addressin, serglycin, osteopontin and class II invariant chain), E- and L-selectin (Dimitroff et. al., PNAS 2000, 97:13841-6 and Dimitroff et. al., J Cell Biol 2001, 153:1277-86) and aggrecan (Fujimoto et. al., Int Immunol 2001, 13:359-66) may also interact with the CD44 receptor. Marked accumulation of CD44, and sometimes hyaluronic acid, is detected in areas of intensive cell migration and cell proliferation, such as in wound healing, tissue remodeling, inflammation (including auto inflammation), morphogenesis and carcinogenesis. The juxtamembrane portion of the cytoplasmic tail of CD44 binds to members of the ezrin-radixin-moesin (ERM) family of actin linker molecules, thus providing a connection between cell surface bound CD44 and the actin cytoskeleton (Tsukita et. al., J Cell Biol 1994, 126: 391-401), thus establishing the basis for CD44-dependent cellular motility.

Depending on the species, the CD44 locus contains about 20 coding exons. For example, the Human CD44 gene includes a total of 19 exons, while the mouse CD44 gene includes 20 exons. The exons of CD44 may be classified into two classes: constant exons and variable exons. The constant exons of both human and mouse include exons $C_1$-$C_5$ at the 5' terminus and $C_6$-$C_9$ at the 3' terminus and encode for the so-called constant regions of CD44 (Screaton et. al., PNAS 1992, 89: 12160-4; Tölg et. al., Neucleic Acids Res, 1993 21:1225-9; Screaton et. al., J Biol Chem 1993, 268: 12235-8). The variable exons are located in the middle of the molecule and include 9 exons in humans (exons $V_2$-$V_{10}$) and 10 exons in mice (exons $V_1$-$V_{10}$). The variable exons encode for the variable regions of CD44. The main molecular species expressed in cells is the standard, hematopoietic, form of CD44 (also named CD44s or CD44H), which is the shortest form of CD44 and is encoded by a mRNA (messenger ribonucleic acid) consisting exclusively of constant exons. Retention of different combinations of variable exons in the mRNA results in a myriad of CD44 splice variants (CD44v, reviewed in Gunthert, Curr. Top Microbiol Immunol 1993, 184:47-63). However, although in theory more than 1,000 individual splice variants may be produced this way, and even in cases where multiple splice variants are co-expressed in one tissue or cell type, CD44s remains the main isoform (for example, Ni et. al., J. Lab. Clin. Med 2002, 139: 59-65; Bell et. al. MCB 1998, 18:5930-41). Under various circumstances and conditions, splicing patterns of CD44 are often altered (such as for example in Gunthert et. al., Cell 1991, 65:13-24; Heider et. al., J Cell Biol 1993, 120:227-33; Wielenga et. al., Cancer Res 1993, 53:4754-6). CD44 transcripts may be produced which contain additional exons; for example, unskipped exons V3, V5, V6 and V7 are known to be expressed by activated lymphocytes and metastatic variants of tumor cells (Naor et al, Crit Rev Clin Lab Sci, 2002, 39:527-79). The cell's choice of the CD44 splice variant is the main determinant for the binding affinity (Lesley et. al., J Exp Med 1995 182:431-7, Stamenkovic et. al. Embo J 1991 10: 343-8, Van der Voort et al., Biochem Biophys Res Commun 1995 214: 135-144).

Expression of various CD44 splice variants in several disease conditions, such as autoimmune diseases, was studied and has been proposed as a target for both diagnoses and treatment in such diseases. Monoclonal antibodies (mAbs) directed against various variant regions of CD44 were suggested as potential agents for treatment of autoimmune diseases. Reber et. al. describe mAbs directed against metastasis-specific variants of CD44V surface protein of a rat pancreatic adenocarcinoma (Reber et. al. Int J. Cancer, 1990, 46:919-27). Anti-CD44 monoclonal antibodies, which inhibit T-cell proliferation, were also provided for treatment of various autoimmune diseases (Rothman et. al. J Immunol. 1991 147:2493-9). Monoclonal antibodies specific for variant forms of CD44 containing exon v6 were also reported as being useful for diagnosing lymphoma (Ristamaki et. al. Blood, 1994, 84:238-43). In addition, it has been reported (Haynes et. al. Arthritis Rheum, 1991, 34:1434-43) that administration of a CD44 protein, peptide or derivative can be used for treating various autoimmune diseases. CD44 expression is also a known target for anti-tumor and anti-inflammatory therapies. Experiments in animals have shown that targeting of CD44 by antibodies, antisense oligos and CD44-soluble proteins markedly reduce the malignant activities of various neoplasms. Antisense strategies and various oligonucleotide-based therapies directed against CD44 expression have been developed, such as described for example in U.S. Pat. No. 6,150,162 and U.S. Pat. No. 5,990,299.

There is some evidence that CD44 and some of its splice variants are involved in autoimmune and pathogen induced neurological disorders, such as, for example, Multiple Sclerosis (MS) and Human T-cell lymphotropic virus type I (HTLV-I)-associated myelopathy/tropical spastic paraparesis (HAM/TSP). Studies of a mice strain with Experimental Allergic Encephalomyelitis (EAE), frequently used as an animal model of Multiple Sclerosis, show that CD44 is induced in vivo on glial cells surrounding inflammatory lesions. (Haegel et. al., J Cell Biol. 1993, 122:1067-77). Mononuclear cells which express the CD44V10 splice variant were detected in the spinal cord of EAE mice (Laman et. al., Mult Scler. 1998, 4:147-53). Animals vaccinated with CD44V3-V10 cDNA developed significantly less severe EAE when compared with sham vaccinated animals or animals vaccinated with CD44s cDNA. (Garin et. al., J Neurol Sci. 2007, 258:17-26). In vivo treatment with an antibody against CD44s did not affect the disease burden whereas combined treatment with antibodies against the isoforms containing the variable regions 6, 7 and 10 (CD44V6, V7 and V10), reduced the disease burden considerably (Laman et. al., Mult. Scler. 1998, 4:147-53).

Human T-cell lymphotropic virus type I (HTLV-I)-associated myelopathy/tropical spastic paraparesis (HAM/TSP) is caused by HTLV-I infection and characterized by spastic paraparesis and urinary disturbance with perivascular HTLV-I-infected and activated CD4+ T-cell infiltration. A CD44 splice variant which contain a direct connection between exons V6 and V10 (CD44V6/V10) was found to be frequently expressed in peripheral blood mononuclear cells of patients of HAM/TSP, (Matsuoka et. al., J Neuroimmunol. 2000, 102: 1-7) These findings led to speculation that the V6/V10-containing lymphocytes are able to migrate into the CNS with ease even at early stages of the disease (Matsuoka et. al., J Neuroimmunol. 2000, 102:1-7).

The "classic" neurodegenerative disorders (such as Alzheimer's disease (AD), Parkinson's Diseases (PD) and Amyotrophic Lateral Sclerosis (ALS)) are adult onset, chronic, progressive and irreversible severely disabling diseases. Additional, non-autoimmune neurodegenerative disorders may include, for example, motor neuron disorders (MND), such as, for example, but not limited to: primary lateral sclerosis (PLS) and Spinal Muscular Atrophy (SMA). Alzheimer's disease (AD) is characterized by progressive mental and cognitive deterioration with consequent formation of amyloid plaques, neurofibrillary tangles, gliosis and neuronal loss. The disease occurs in both genetic and sporadic forms whose clinical course and pathological features are quite similar. Three genes have been identified to date which, when mutated, cause an autosomal dominant form of Alzheimer's disease. These genes encode the Amyloid Protein Precursor (APP) and two structurally and functionally related proteins, presenilin-1 (PS1) and presenilin-2 (PS2). Mutations in any of the three proteins enhance proteolytic processing of APP via an intracellular pathway that produces Amyloid β peptide (Aβ), a 40-42 amino acid long peptide that is the primary component of amyloid plaque in Alzheimer's disease.

Amyotrophic Lateral Sclerosis (ALS) is a progressive lethal neurological disease affecting one to two in every 100,000 people who are diagnosed with ALS each year. ALS occurs when the motor nerve cells that control voluntary movement gradually degenerate. The loss of these motor neurons causes the muscles which they control to weaken and waste away, leading to paralysis and eventually death. The etiology of most ALS cases remains unknown, but 2% of instances are due to mutations in the Cu/Zn superoxide dismutase gene (SOD1). In the latter, mutant SOD1 induces non-cell-autonomous motor neuron killing by an unknown gain of toxicity. Selective vulnerability of motor neurons likely arises from a combination of several mechanisms, including protein misfolding, mitochondrial dysfunction, oxidative damage, defective axonal transport, excitotoxicity, insufficient growth factor signaling, and inflammation. Damage within motor neurons is enhanced by damage incurred by non-neuronal neighboring cells, via an inflammatory response that accelerates disease progression (Boillee et. al. Neuron. 2006, 52:39-59, Pehar et. al., Neurodegener. Dis. 2005, 2:139-46).

Parkinson's disease (PD) is a chronic and progressive neurodegenerative disease caused by a selective degeneration of dopaminergic neurons in the substantia nigra pars compacta of the brain; 80% of the neurons die of an unknown cause before the symptoms appear. Symptoms include intermittent tremor in the limbs, poor balance and difficulty in initiating movement.

Primary Lateral Sclerosis (PLS) is a rare neuromuscular disease characterized by progressive muscle weakness in the voluntary muscles. As a motor neuron disease, PLS usually develops when nerve cells, which control voluntary muscle movement, degenerate and die, causing weakness in the muscles they control. Spinal Muscular Atrophy (SMA) is a term applied to various disorders, all having in common a genetic cause and the manifestation of weakness due to loss of the motor neurons of the spinal cord and brainstem.

Unlike neurological autoimmune diseases (such as multiple sclerosis), in which the innate immune system targets normal neuronal cell constituents through infiltration of T-cells and lymphocytes across the blood brain barrier, in classic neurodegenerative disorders the neurons die of an unknown reason. The role of the neuron-glia interaction and the inflammatory process in classic neurodegenerative diseases has been suggested. Macro and microglial cells have been suggested in having a role in multistep degenerative processes in ALS and respective disease models. The activation of astroglial and microglial cells occurs early in the pathogenesis of the disease and seems to greatly influence disease onset and promotion (Di Giorgio et. al., Nat Neurosci. 2007; 10:608-614; Esposito et. al. Exp Neurol. 2007; Kim et. al., Exp Mol Med. 2006; 38:333-47).

No clear evidence of the role of specific variants of CD44 in Alzheimer disease, Amyotrophic Lateral Sclerosis or Parkinson's disease has been provided. In primary cultures of mouse astrocytes, surface expression and mRNA levels of CD44 could be induced via stimulation with either phorbol ester (PMA), or tumor necrosis factor alpha plus gamma interferon. The CD44 transcripts produced contain additional exons, including the exon v6, as well as variants of larger size. However it is not known if such activation occurs in vivo or in humans in the course of neurodegenerative diseases (Haegel et. al, J Cell Biol, 1993, 122:1067-77). The localization of CD44s was investigated by immunohistochemistry in post-mortem human brain tissue of control subjects and patients with Alzheimer's disease. In gray matter, it was found to be associated with some astrocytes of both protoplasmic and fibrous morphology. In the Alzheimer's disease brain, the number of CD44 positive astrocytes increased dramatically. CD44 may be an important adhesion molecule for these astrocytic processes (Akiyama et. al., Brain Res. 1993, 632:249-59). However, it is not known if cells expressing CD44 participate in the disease progress or are helping to prevent neurodegeneration. No CD44 splice variants were described in these diseases.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiments, there are provided CD44 splice variants whose expression is elevated in biological samples obtained from patients diagnosed with classical neurodegenerative diseases such as Amyotrophic Lateral Sclerosis (ALS) and Alzheimer disease (AD). Of the CD44 splice variants provided, some of variants that contain a single variant exon, are novel variants not previously described. There are further provided CD44 polypeptides, polynucleotides encoding the same, and antibodies and oligonucleotides directed thereagainst, which may be used in treatment and diagnosis of neurodegenerative diseases.

According to some embodiments, there is provided a method of diagnosing or monitoring neurodegenerative disease in a patient; the method includes detecting the expression level of a nucleic acid in a biological sample of the patient, wherein the nucleic includes a contiguous nucleotide sequence being at least 90% homologous to at least 20 nucleotides of: SEQ ID NO: 1, SEQ ID NO:3, SEQ ID NO:5, SEQ ID NO:7, or any combination thereof.

According to further embodiments, the contiguous nucleotide sequence being at least 90% homologous to at least 20 nucleotides of SEQ ID NO: 1 may include: a contiguous nucleotide sequence being at least 90% homologous to coordinates 1-1212 of SEQ ID NO:1, a contiguous nucleotide sequence being at least 90% homologous to coordinates 639-822 of SEQ ID NO:1, a contiguous nucleotide sequence being at least 90% homologous to coordinates 639-696 of SEQ ID NO:1, a contiguous nucleotide sequence being at least 90% homologous to coordinates 766-822 of SEQ ID NO:1, or any combination thereof. The contiguous nucleotide sequence being at least 90% homologous to at least 20 nucleotides of SEQ ID NO: 3 may include: a contiguous nucleotide sequence being at least 90% homologous to coordinates 1-1215 of SEQ ID NO:3, a contiguous nucleotide sequence being at least 90% homologous to coordinates 639-825 of SEQ ID NO:3, a contiguous nucleotide sequence being at least 90% homologous to coordinates 639-696 of SEQ ID NO:3, a contiguous nucleotide sequence being at least 90% homologous to coordinates 769-825 of SEQ ID NO:3, or any combination thereof. The contiguous nucleotide sequence being at least 90% homologous to at least 20 nucleotides of SEQ ID NO:5 may include: a contiguous nucleotide sequence being at least 90% homologous to coordinates 1-1218 of SEQ ID NO:5, a contiguous nucleotide sequence being at least 90% homologous to coordinates 639-828 of SEQ ID NO:5, a contiguous nucleotide sequence being at least 90% homologous to coordinates 639-696 of SEQ ID NO:5, a contiguous nucleotide sequence being at least 90% homologous to coordinates 772-828 of SEQ ID NO:5, or any combination thereof. The contiguous nucleotide sequence being at least 90% homologous to at least 20 nucleotides of SEQ ID NO: 7 may include: a contiguous nucleotide sequence being at least 90% homologous to coordinates 1-1290 of SEQ ID NO:7, a contiguous nucleotide sequence being at least 90% homologous to coordinates 639-900 of SEQ ID NO:7, a contiguous nucleotide sequence being at least 90% homologous to coordinates 639-696 of SEQ ID NO:7, a contiguous nucleotide sequence being at least 90% homologous to coordinates 844-900 of SEQ ID NO:7, or any combination thereof.

According to further embodiments, the neurodegenerative disease may include Amyotrophic Lateral Sclerosis (ALS), Parkinson's disease (PD), Alzheimer's disease (AD), Primary Lateral Sclerosis (PLS), Spinal Muscular Atrophy (SMA), or any combination thereof.

According to yet additional embodiments, the biological sample may include a cell, a tissue, a biological fluid, or any combination thereof.

According to further embodiments, the expression level of the nucleic acid may be detected by determining expression level of a ribonucleic acid (RNA) encoded by the nucleic acid.

The method may further include isolating the RNA from the biological sample prior to detecting said RNA level expressed by said nucleic acid.

According to yet additional embodiments, the expression level of the RNA may be detected by Polymerase Chain Reaction (PCR), Reverse-Transcriptase-PCR (RT-PCR), Northern Blot, Real-time PCR, or any combination thereof. The expression level of the RNA may be detected by hybridization to an oligonucleotide. The oligonucleotide may include deoxyribonucleic acid (DNA), RNA, complementary deoxyribonucleic acid (cDNA), genomic DNA, synthetic oligonucleotide, or any combination thereof.

According to some embodiments, there is provided a method of diagnosing or monitoring neurodegenerative disease in a patient; the method includes detecting the expression of a polypeptide in a biological sample of the patient, wherein said polypeptide is selected from a group that includes a contiguous amino acid sequence being at least 90% homologous to at least 10 amino acid of: SEQ ID NO: 2, SEQ ID NO: 4, SEQ ID NO: 6, SEQ ID NO: 8, or any combination thereof.

According to further embodiments, the contiguous amino acid sequence being at least 90% homologous to at least 10 amino acid of SEQ ID NO: 2 may include a contiguous amino acid sequence being at least 90% homologous to amino acid coordinates 1-403 of SEQ ID NO:2, a contiguous amino acid sequence being at least 90% homologous to amino acid coordinates 214-274 of SEQ ID NO:2, a contiguous amino acid sequence being at least 90% homologous to amino acid coordinates 214-232 of SEQ ID NO:2, a contiguous amino acid sequence being at least 90% homologous to amino acid coordinates 256-274 of SEQ ID NO:2, or any combination thereof. The contiguous amino acid sequence being at least 90% homologous to at least 10 amino acid of: SEQ ID NO: 4 may include a contiguous amino acid sequence being at least 90% homologous to amino acid coordinates 1-404 of SEQ ID NO:4, a contiguous amino acid sequence being at least 90% homologous to amino acid coordinates 214-275 of SEQ ID NO:4, a contiguous amino acid sequence being at least 90% homologous to amino acid coordinates 214-232 of SEQ ID NO:4, a contiguous amino acid sequence being at least 90% homologous to amino acid coordinates 257-275 of SEQ ID NO:4, or any combination thereof. The contiguous amino acid sequence being at least 90% homologous to at least 10 amino acid of: SEQ ID NO: 6 may include a contiguous amino acid sequence being at least 90% homologous to amino acid coordinates 1-405 of SEQ ID NO:6, a contiguous amino acid sequence being at least 90% homologous to amino acid coordinates 214-276 of SEQ ID NO:6, a contiguous amino acid sequence being at least 90% homologous to amino acid coordinates 214-232 of SEQ ID NO:6, a contiguous amino acid sequence being at least 90% homologous to amino acid coordinates 258-276 of SEQ ID NO:6, or any combination thereof. The contiguous amino acid sequence being at least 90% homologous to at least 10 amino acid of: SEQ ID NO: 8 may include: a contiguous amino acid sequence being at least 90% homologous to amino acid coordinates 1-429 of SEQ ID NO:8, a contiguous amino acid sequence being at least 90% homologous to amino acid coordinates 214-300 of SEQ ID NO:8, a contiguous amino acid sequence being at least 90% homologous to amino acid coordinates 214-232 of SEQ ID NO:8, a contiguous amino acid sequence being at least 90% homologous to amino acid coordinates 282-300 of SEQ ID NO:8, or any combination thereof.

According to further embodiments, the neurodegenerative disease may include Amyotrophic Lateral Sclerosis (ALS), Parkinson's disease (PD), Alzheimer's disease (AD), Primary Lateral Sclerosis (PLS), Spinal Muscular Atrophy (SMA), or any combination thereof.

According to yet additional embodiments, the biological sample may include a cell, a tissue, a biological fluid, or any combination thereof.

According to additional embodiments, detecting may include detecting immuno-complexes of the polypeptide and an antibody adapted to specifically bind said polypeptide. Detecting the immuno-complexes may include Western Blot, immunohistochemistry, immunocytochemistry, enzyme linked immunosorbent assay (ELISA), or any combination thereof. The antibody may include a monoclonal antibody, a polyclonal antibody, or any combination thereof.

According to some embodiments, there is provided a method of treating or preventing a neurodegenerative disease, the method may include administration of a composition comprising a reagent capable of modulating expression of ribonucleic acid (RNA) encoded by a nucleic acid, wherein said nucleic acid may include a contiguous nucleotide sequence being at least 90% homologous to at least 20 nucleotides of: SEQ ID NO: 1, SEQ ID NO: 3, SEQ ID NO: 5, SEQ ID NO: 7, or any combination thereof.

According to further embodiments, the contiguous nucleotide sequence being at least 90% homologous to at least 20 nucleotides of SEQ ID NO: 1 may include: a contiguous nucleotide sequence being at least 90% homologous to coordinates 1-1212 of SEQ ID NO:1, a contiguous nucleotide sequence being at least 90% homologous to coordinates 639-822 of SEQ ID NO:1, a contiguous nucleotide sequence being at least 90% homologous to coordinates 639-696 of SEQ ID NO:1, a contiguous nucleotide sequence being at least 90% homologous to coordinates 766-822 of SEQ ID NO:1, or any combination thereof. The contiguous nucleotide sequence being at least 90% homologous to at least 20 nucleotides of SEQ ID NO: 3 may include: a contiguous nucleotide sequence being at least 90% homologous to coordinates 1-1215 of SEQ ID NO:3, a contiguous nucleotide sequence being at least 90% homologous to coordinates 639-825 of SEQ ID NO:3, a contiguous nucleotide sequence being at least 90% homologous to coordinates 639-696 of SEQ ID NO:3, a contiguous nucleotide sequence being at least 90% homologous to coordinates 769-825 of SEQ ID NO:3, or any combination thereof. The contiguous nucleotide sequence being at least 90% homologous to at least 20 nucleotides of SEQ ID NO:5 may include: a contiguous nucleotide sequence being at least 90% homologous to coordinates 1-1218 of SEQ ID NO:5, a contiguous nucleotide sequence being at least 90% homologous to coordinates 639-828 of SEQ ID NO:5, a contiguous nucleotide sequence being at least 90% homologous to coordinates 639-696 of SEQ ID NO:5, a contiguous nucleotide sequence being at least 90% homologous to coordinates 772-828 of SEQ ID NO:5, or any combination thereof. The contiguous nucleotide sequence being at least 90% homologous to at least 20 nucleotides of SEQ ID NO: 7 may include: a contiguous nucleotide sequence being at least 90% homologous to coordinates 1-1290 of SEQ ID NO:7, a contiguous nucleotide sequence being at least 90% homologous to coordinates 639-900 of SEQ ID NO:7, a contiguous nucleotide sequence being at least 90% homologous to coordinates 639-696 of SEQ ID NO:7, a contiguous nucleotide sequence being at least 90% homologous to coordinates 844-900 of SEQ ID NO:7, or any combination thereof.

According to further embodiments, the administration may include administration to a patient, a cell of a patient, a tissue of a patient, or any combination thereof. Modulating may include attenuating the expression of the RNA encoded by the nucleic acid, increasing the expression of the RNA encoded by the nucleic acid, or both.

According to yet additional embodiments, the reagent may include one or more polynucleotides, capable of hybridizing with said nucleic acid. The one or more polynucleotide may include deoxyribonucleic acid (DNA), RNA, small interfering RNA (siRNA), or any combination thereof. The siRNA may include a first polynucleotide sequence hybridized to a second polynucleotide sequence that is complimentary to said first polynucleotide sequence, and wherein said first polynucleotide sequence is a contiguous span of at least 15 nucleotides at least 15 nucleotides of a contiguous nucleotide sequence being at least 90% homologous to at least 20 nucleotides of: SEQ ID NO: 1, SEQ ID NO:3, SEQ ID NO:5 or SEQ ID NO:7.

According to additional embodiments, the reagent capable of modulating the expression of the ribonucleic acid may include a small molecule entity (SME). The small molecule entity may include a modulator of the ERK-MAP kinase pathway, modulator of the PKC Kinase, and the like.

According to some embodiments, there is further provided a method of treating or preventing a neurodegenerative disease, the method includes administration of a composition comprising a reagent capable of modulating expression and/or activity of a polypeptide, wherein the sequence of said polypeptide may include a contiguous amino acid sequence being at least 90% homologous to at least 10 amino acid of: SEQ ID NO: 2, SEQ ID NO: 4, SEQ ID NO: 6, SEQ ID NO: 8, or any combination thereof.

According to additional embodiments, the contiguous amino acid sequence being at least 90% homologous to at least 10 amino acid of SEQ ID NO: 2 may include a contiguous amino acid sequence being at least 90% homologous to amino acid coordinates 1-403 of SEQ ID NO:2, a contiguous amino acid sequence being at least 90% homologous to amino acid coordinates 214-274 of SEQ ID NO:2, a contiguous amino acid sequence being at least 90% homologous to amino acid coordinates 214-232 of SEQ ID NO:2, a contiguous amino acid sequence being at least 90% homologous to amino acid coordinates 256-274 of SEQ ID NO:2, or any combination thereof. The contiguous amino acid sequence being at least 90% homologous to at least 10 amino acid of: SEQ ID NO: 4 may include a contiguous amino acid sequence being at least 90% homologous to amino acid coordinates 1-404 of SEQ ID NO:4, a contiguous amino acid sequence being at least 90% homologous to amino acid coordinates 214-275 of SEQ ID NO:4, a contiguous amino acid sequence being at least 90% homologous to amino acid coordinates 214-232 of SEQ ID NO:4, a contiguous amino acid sequence being at least 90% homologous to amino acid coordinates 257-275 of SEQ ID NO:4, or any combination thereof. The contiguous amino acid sequence being at least 90% homologous to at least 10 amino acid of: SEQ ID NO: 6 may include a contiguous amino acid sequence being at least 90% homologous to amino acid coordinates 1-405 of SEQ ID NO:6, a contiguous amino acid sequence being at least 90% homologous to amino acid coordinates 214-276 of SEQ ID NO:6, a contiguous amino acid sequence being at least 90% homologous to amino acid coordinates 214-232 of SEQ ID NO:6, a contiguous amino acid sequence being at least 90% homologous to amino acid coordinates 258-276 of SEQ ID NO:6, or any combination thereof. The contiguous amino acid sequence being at least 90% homologous to at least 10 amino acid of: SEQ ID NO: 8 may include: a contiguous amino acid sequence being at least 90% homologous to amino acid coordinates 1-429 of SEQ ID NO:8, a contiguous amino acid sequence being at least 90% homologous to amino acid coordinates 214-300 of SEQ ID NO:8, a contiguous amino acid sequence being at least 90% homologous to amino acid coordinates 214-232 of SEQ ID NO:8, a contiguous amino acid sequence being at least 90% homologous to amino acid coordinates 282-300 of SEQ ID NO:8, or any combination thereof.

According to further embodiments, the administration may include administration to a patient, a cell of a patient, a tissue of a patient, or any combination thereof. Modulating may include attenuating the expression and/or activity of the polypeptide, increasing the expression ad/or activity of the polypeptide, or both.

According to additional embodiments, the reagent may include an antibody adapted to specifically bind the polypeptide. The antibody may include a monoclonal antibody, a polyclonal antibody, or any combination thereof.

According to some embodiments, there is provided an isolated polynucleotide molecule, the sequence of which includes SEQ ID NO: 3. There is further provided the complement of the isolated polynucleotide molecule, wherein the complement and the polynucleotide are 100% complementary. According to other embodiments, there is further provided a first polynucleotide derived from the isolated polynucleotide molecule wherein the first polynucleotide includes a contiguous first nucleotide sequence being at least 90% homologous to nucleotide coordinates 639-825 of SEQ ID NO:3. There is further provided a second polynucleotide derived from the isolated polynucleotide molecule wherein the second polynucleotide comprises a contiguous second nucleotide sequence being at least 90% homologous to nucleotide coordinates 639-696 of SEQ ID NO:3. There is yet further provided a third polynucleotide derived from the isolated polynucleotide molecule wherein the third polynucleotide comprises a contiguous third nucleotide sequence being at least 90% homologous to nucleotide coordinates 769-825 of SEQ ID NO:3.

According to further embodiments, the isolated polynucleotide molecule of the SEQ ID NO: 3 may encode for a polypeptide, the sequence of which includes SEQ ID NO:4. There is further provided a first peptide derived from the polypeptide of SEQ ID NO:4, wherein said first peptide includes a contiguous first amino acid sequence being at least 90% homologous to amino acid coordinates 214-275 of SEQ ID NO:4. There is further provided a second peptide derived from the polypeptide of SEQ ID NO:4, wherein said second peptide includes a contiguous first amino acid sequence being at least 90% homologous to amino acid coordinates 214-232 of SEQ ID NO:4. There is further provided a third peptide derived from the polypeptide of SEQ ID NO:4, wherein said third peptide includes a contiguous first amino acid sequence being at least 90% homologous to amino acid coordinates 257-275 of SEQ ID NO:4. According to some embodiments, the polypeptide expression is elevated in biological samples from patients diagnosed with neurodegenerative disease. The polypeptide is a CD44 variant. The neurodegenerative disease may include Amyotrophic Lateral Sclerosis (ALS), Parkinson's disease (PD), Alzheimer's disease (AD), Primary Lateral Sclerosis (PLS), Spinal Muscular Atrophy (SMA), or any combination thereof.

According to some embodiments, there is provided an isolated polynucleotide molecule, the sequence of which includes SEQ ID NO: 5. There is further provided the complement of the isolated polynucleotide molecule, wherein the complement and the polynucleotide are 100% complementary. According to other embodiments, there is further provided a first polynucleotide derived from the isolated polynucleotide molecule, wherein the first polynucleotide includes a contiguous first nucleotide sequence being at least 90% homologous to nucleotide coordinates 639-828 of SEQ ID NO:5. There is further provided a second polynucleotide derived from the isolated polynucleotide molecule, wherein the second polynucleotide includes a contiguous first nucleotide sequence being at least 90% homologous to nucleotide coordinates 639-696 of SEQ ID NO:5. There is further provided a third polynucleotide derived from the isolated polynucleotide molecule, wherein the third polynucleotide comprises a contiguous third nucleotide sequence being at least 90% homologous to nucleotide coordinates 772-828 of SEQ ID NO:5.

According to further embodiments, the isolated polynucleotide molecule of the SEQ ID NO: 5 may encode for a polypeptide, the sequence of which includes SEQ ID NO:6. According to additional embodiments, there is further provided a first peptide derived from the polypeptide of SEQ ID NO: 6, wherein the first peptide includes a contiguous first amino acid sequence being at least 90% homologous to amino acid coordinates 214-276 of SEQ ID NO:6. There is further provided a second peptide derived from the polypeptide of SEQ ID NO: 6, wherein the second peptide includes a contiguous second amino acid sequence being at least 90% homologous to amino acid coordinates 214-232 of SEQ ID NO:6. There is further provided a third peptide derived from the polypeptide of SEQ ID NO: 6, wherein the third peptide includes a contiguous third amino acid sequence being at least 90% homologous to amino acid coordinates 258-276 of SEQ ID NO:6. According to some embodiments, the polypeptide expression is elevated in biological samples from patients diagnosed with neurodegenerative disease. The polypeptide may include a CD44 variant. The neurodegenerative disease may include Amyotrophic Lateral Sclerosis (ALS), Parkinson's disease (PD), Alzheimer's disease (AD), Primary Lateral Sclerosis (PLS), Spinal Muscular Atrophy (SMA), or any combination thereof.

According to some embodiments, there is provided a kit for diagnosing a neurodegenerative disease, the kit includes at least one reagent capable of detecting the expression of a nucleic acid in a biological sample, wherein the nucleic acid may include a contiguous nucleotide sequence being at least 90% homologous to at least 20 nucleotides of: SEQ ID NO: 1, SEQ ID NO: 3, SEQ ID NO: 5, SEQ ID NO: 7, or any combination thereof. According to further embodiments, the contiguous nucleotide sequence being at least 90% homologous to at least 20 nucleotides of SEQ ID NO: 1 may include: a contiguous nucleotide sequence being at least 90% homologous to coordinates 1-1212 of SEQ ID NO:1, a contiguous nucleotide sequence being at least 90% homologous to coordinates 639-822 of SEQ ID NO:1, a contiguous nucleotide sequence being at least 90% homologous to coordinates 639-696 of SEQ ID NO:1, a contiguous nucleotide sequence being at least 90% homologous to coordinates 766-822 of SEQ ID NO:1, or any combination thereof. The contiguous nucleotide sequence being at least 90% homologous to at least 20 nucleotides of SEQ ID NO: 3 may include: a contiguous nucleotide sequence being at least 90% homologous to coordinates 1-1215 of SEQ ID NO:3, a contiguous nucleotide sequence being at least 90% homologous to coordinates 639-825 of SEQ ID NO:3, a contiguous nucleotide sequence being at least 90% homologous to coordinates 639-696 of SEQ ID NO:3, a contiguous nucleotide sequence being at least 90% homologous to coordinates 769-825 of SEQ ID NO:3, or any combination thereof. The contiguous nucleotide sequence being at least 90% homologous to at least 20 nucleotides of SEQ ID NO:5 may include: a contiguous nucleotide sequence being at least 90% homologous to coordinates 1-1218 of SEQ ID NO:5, a contiguous nucleotide sequence being at least 90% homologous to coordinates 639-828 of SEQ ID NO:5, a contiguous nucleotide sequence being at least 90% homologous to coordinates 639-696 of SEQ ID NO:5, a contiguous nucleotide sequence being at least 90% homologous to coordinates 772-828 of SEQ ID NO:5, or any combination thereof. The contiguous nucleotide sequence being at least 90% homologous to at least 20 nucleotides of SEQ ID NO: 7 may include: a contiguous nucleotide sequence being at least 90% homologous to coordinates 1-1290 of SEQ ID NO:7, a contiguous nucleotide sequence being at least 90% homologous to coordinates 639-900 of SEQ ID NO:7, a contiguous nucleotide sequence being at least 90% homologous to coordinates 639-696 of SEQ ID NO:7, a contiguous nucleotide sequence being at least 90% homologous to coordinates 844-900 of SEQ ID NO:7, or any combination thereof. According to further embodiments, the neurodegenerative disease may include: Amyotrophic Lateral Sclerosis (ALS), Parkinson's disease (PD), Alzheimer's disease (AD), Primary Lateral Sclerosis (PLS), Spinal Muscular Atrophy (SMA), or any combination thereof. The biological sample may include a cell, a tissue, a body fluid, or any combination thereof.

According to yet additional embodiments, the at least one reagent may include an oligonucleotide that is capable of hybridizing with said nucleic acid or with a ribonucleic acid (RNA) molecule encoded by said nucleic acid. The oligonucleotide may include DNA, RNA, cDNA, genomic DNA, synthetic oligonucleotides, or any combination thereof.

According to some embodiments, there is provided a kit for diagnosing a neurodegenerative disease, comprising at least one reagent capable of detecting the expression of a polypeptide in a biological sample, wherein the polypeptide includes a contiguous amino acid sequence being at least 90% homologous to at least 10 amino acid of: SEQ ID NO: 2, SEQ ID NO: 4, SEQ ID NO: 6, SEQ ID NO: 8, or any combination thereof. According to additional embodiments, the contiguous amino acid sequence being at least 90% homologous to at least 10 amino acid of SEQ ID NO: 2 may include a contiguous amino acid sequence being at least 90% homologous to amino acid coordinates 1-403 of SEQ ID NO:2, a contiguous amino acid sequence being at least 90% homologous to amino acid coordinates 214-274 of SEQ ID NO:2, a contiguous amino acid sequence being at least 90% homologous to amino acid coordinates 214-232 of SEQ ID NO:2, a contiguous amino acid sequence being at least 90% homologous to amino acid coordinates 256-274 of SEQ ID NO:2, or any combination thereof. The contiguous amino acid sequence being at least 90% homologous to at least 10 amino acid of: SEQ ID NO: 4 may include a contiguous amino acid sequence being at least 90% homologous to amino acid coordinates 1-404 of SEQ ID NO:4, a contiguous amino acid sequence being at least 90% homologous to amino acid coordinates 214-275 of SEQ ID NO:4, a contiguous amino acid sequence being at least 90% homologous to amino acid coordinates 214-232 of SEQ ID NO:4, a contiguous amino acid sequence being at least 90% homologous to amino acid coordinates 257-275 of SEQ ID NO:4, or any combination thereof. The contiguous amino acid sequence being at least 90% homologous to at least 10 amino acid of: SEQ ID NO: 6 may include a contiguous amino acid sequence being at least 90% homologous to amino acid coordinates 1-405 of SEQ ID NO:6, a contiguous amino acid sequence being at least 90% homologous to amino acid coordinates 214-276 of SEQ ID NO:6, a contiguous amino acid sequence being at least 90% homologous to amino acid coordinates 214-232 of SEQ ID NO:6, a contiguous amino acid sequence being at least 90% homologous to amino acid coordinates 258-276 of SEQ ID NO:6, or any combination thereof. The contiguous amino acid sequence being at least 90% homologous to at least 10 amino acid of: SEQ ID NO: 8 may include: a contiguous amino acid sequence being at least 90% homologous to amino acid coordinates 1-429 of SEQ ID NO:8, a contiguous amino acid sequence being at least 90% homologous to amino acid coordinates 214-300 of SEQ ID NO:8, a contiguous amino acid sequence being at least 90% homologous to amino acid coordinates 214-232 of SEQ ID NO:8, a contiguous amino acid sequence being at least 90% homologous to amino acid coordinates 282-300 of SEQ ID NO:8, or any combination thereof. According to further embodiments, the neurodegenerative disease may include: Amyotrophic Lateral Sclerosis (ALS), Parkinson's disease (PD), Alzheimer's disease (AD), Primary Lateral Sclerosis (PLS), Spinal Muscular Atrophy (SMA), or any combination thereof. The biological sample may include a cell, a tissue, a body fluid, or any combination thereof.

According to further embodiments, the at least one reagent may include an antibody adapted to specifically interact with said polypeptide and to form detectable immuno-complexes. The antibody may include a monoclonal antibody, polyclonal antibody, or any combination thereof.

In addition to the exemplary aspects and embodiments described above, further aspects and embodiments will become apparent by reference to the figures and by study of the following detailed descriptions.

BRIEF DESCRIPTION OF THE FIGURES

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIG. 2 schematically illustrates the nucleotide and protein sequences of the V3 variant exon and splice junctions of V3 variant exons with constant exons C5 and C6;

FIG. 3 schematically illustrates the nucleotide and protein sequences of the V6 variant exon and splice junctions of V6 variant exons with constant exons C5 and C6;

FIG. 4 schematically illustrates the nucleotide and protein sequences of the V7 variant exon and splice junctions of V7 variant exons with constant exons C5 and C6;

FIG. 5 schematically illustrates the nucleotide and protein sequences of the V10 variant exon and splice junctions of V10 variant exons with constant exons C5 and C6;

DETAILED DESCRIPTION

Figure 1:
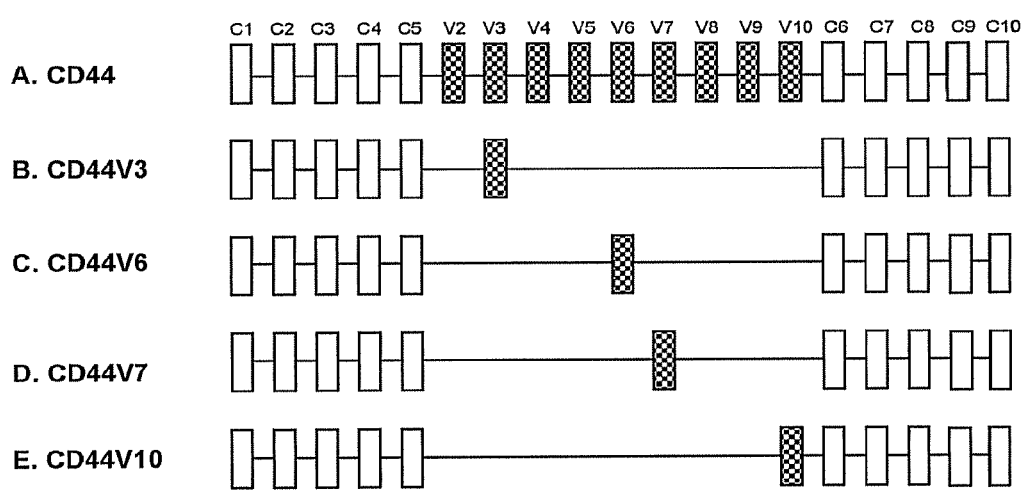
FIG. 1 schematically illustrates the genomic structure of CD44.

In the following description, various aspects of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention.

According to some embodiments, there are provided CD44 splice variants whose expression is upregulated in biological samples obtained from patients diagnosed with classical neurodegenerative diseases such as Amyotrophic Lateral Sclerosis (ALS) and Alzheimer disease (AD). There are further provided CD44 polypeptides, polynucleotides encoding the same, and antibodies and oligonucleotides directed thereagainst, which may be used in treatment and diagnosis of neurodegenerative diseases.

The following are terms which are used throughout the description and which should be understood in accordance with the various embodiments to mean as follows:

As referred to herein, the term "CD44 gene", relates to the gene sequence and/or gene structure of the CD44, which is schematically illustrated in FIG. 1A.

As referred to herein, the term "CD44 splice variants nucleic acid sequences", interchangeably referred to also as the "CD44 variants coding sequences" or "CD44 variants" or "CD44 splice variant transcript" may relate to one or more of the CD44 splice variants, which are described hereinbelow.

As referred to herein, the term "CD44 splice variant V3 nucleic acid coding sequence" interchangeably referred to also as "CD44 splice variant V3 coding sequence" or "CD44V3" or "CD44V3 transcript" or "CD44V3 coding sequence" or "CD44 splice variant V3", may relate to nucleic acid molecules having the sequence shown in SEQ ID NO: 1, nucleic acid molecules having at least 90% identity (see below) to said sequence and fragments (see below) of the above molecules of at least 20 nucleotides long. This molecule comprises sequences coding for a naturally occurring, alternative splice variant of the native and known CD44 transcript. The CD44V3, schematically represented in FIG. 1B, includes at least constant exon C5, variant exon V3 and constant exon C6, and more preferably includes constant exons C1-C5, C6-C9 as well as variable exons V3 of the CD44 gene. FIG. 2A lists the nucleotide sequence of variant exon V3. FIG. 2B lists the nucleotide sequence of the junction bridges between constant exon C5 and variant exon V3. FIG. 2C lists the nucleotide sequence of the junction bridges between variant exon V3 and constant exon C6.

As referred to herein, the term "CD44 splice variant V6 nucleic acid coding sequence" interchangeably referred to also as "CD44 splice variant V6 coding sequence" or "CD44V6" or "CD44V6 transcript" or "CD44V6 coding sequence" or "CD44 splice variant V6", may relate to nucleic acid molecules having the sequence shown in SEQ ID NO: 3, nucleic acid molecules having at least 90% identity (see below) to said sequence and fragments (see below) of the above molecules of at least 20 nucleotides long. This molecule comprises sequences coding for a novel, alternative splice variant of the native and known CD44 transcript. The CD44V6, schematically represented in FIG. 1C, includes at least constant exon C5, variant exon V6 and Constant exon C6 and more preferably includes constant exons C1-C5, C6-C9 as well as variable exons V6 of the CD44 gene. FIG. 3A lists the nucleotide sequence of variant exon V6. FIG. 3B lists the nucleotide sequence of the junction bridges between constant exon C5 and variant exon V6. FIG. 3C lists the nucleotide sequence of the junction bridges between variant exon V6 and constant exon C6.

As referred to herein, the term "CD44 splice variant V7 nucleic acid coding sequence" interchangeably referred to also as "CD44 splice variant V7 coding sequence" or "CD44V7" or "CD44V7 transcript" or "CD44V7 coding sequence" or "CD44 splice variant V7", may relate to nucleic acid molecules having the sequence shown in SEQ ID NO: 5, nucleic acid molecules having at least 90% identity (see below) to said sequence and fragments (see below) of the above molecules of at least 20 nucleotides long. This molecule comprises sequences coding for a novel, naturally occurring, alternative splice variant of the native and known CD44 transcript. The CD44V7, schematically represented in FIG. 1D, includes at least constant exon C5, variant exon V7 and constant exon C6, and more preferably includes constant exons C1-C5, C6-C9 as well as variable exons V7 of the CD44 gene. FIG. 4A lists the nucleotide sequence of variant exon V7. FIG. 4B lists the nucleotide sequence of the junction bridges between constant exon C5 and variant exon V7. FIG. 4C lists the nucleotide sequence of the junction bridges between variant exon V7 and constant exon C6.

As referred to herein, the term "CD44 splice variant V10 nucleic acid coding sequence" interchangeably referred to also as "CD44 splice variant V10 coding sequence", or "CD44V10", or "CD44V10 transcript" or "CD44V10 coding sequence" or "CD44 splice variant V10" may relate to nucleic acid molecules having the sequence shown in SEQ ID NO: 7, nucleic acid molecules having at least 90% identity (see below) to said sequence and fragments (see below) of the above molecules of at least 20 nucleotides long. This molecule comprises sequences coding for a naturally occurring, alternative splice variant of the native and known CD44 transcript. The CD44V10, schematically represented in FIG. 1E, includes at least constant exon C5, variant exon V10 and constant exon C6, and more preferably includes constant exons C1-C5, C6-C9 as well as variable exons V10 of the CD44 gene. FIG. 5A lists the nucleotide sequence of variant exon V10. FIG. 5B lists the nucleotide sequence of the junction bridges between constant exon C5 and variant exon V10. FIG. 5C lists the nucleotide sequence of the junction bridges between variant exon V10 and constant exon C6.

As referred to herein, the term "CD44 splice variants product", interchangeably referred to also as the "CD44 variants product" or "CD44 variants protein" or "CD44 variants peptide" may relate to one or more of the CD44 splice variant products which are described hereinbelow.

As referred to herein, the term "CD44V3 product", interchangeably referred to also as "CD44V3 protein" or "CD44V3 peptide" is a polypeptide having an amino acid sequence encoded by the CD44V3 coding sequence. By "polypeptide" is intended a peptide or protein, as well as peptides or proteins having chemically modified amino acids (see below) such as a glycopeptide or glycoprotein. The amino acid sequence of CD44V3 product is shown in SEQ ID NO: 2. The amino acid sequence of the C5-V3-C6 region of CD44V3 corresponds to coordinates 214-274 in SEQ ID NO: 2. FIG. 2A lists the amino acid sequence of variant exon V3. FIG. 2B lists the amino acid sequence of the junction bridges between constant exon C5 and variant exon V3. FIG. 2C lists the amino acid sequence of the junction bridges between variant exon V3 and constant exon C6. "CD44V3 product" also includes homologues (see below) of said amino acid sequence in which one or more amino acids have been added, deleted, substituted (see below) or chemically modified (see below), as well as fragments (see below) of this sequence having at least 6 amino acids.

As referred to herein, the term "CD44V6 product", interchangeably referred to also as "CD44V6 protein" or "CD44V6 peptide" is a polypeptide having an amino acid sequence encoded by the CD44V6 coding sequence. By "polypeptide" is intended a peptide or protein, as well as peptides or proteins having chemically modified amino acids (see below) such as a glycopeptide or glycoprotein. The amino acid sequence of CD44V6 product is shown in SEQ ID NO: 4. The amino acid sequence of the C5-V6-C6 region of CD44V6 corresponds to coordinates 214-275 in SEQ ID NO: 4. FIG. 3A lists the amino acid sequence of variant exon V6. FIG. 3B lists the amino acid sequence of the junction bridges between constant exon C5 and variant exon V6. FIG. 3C lists the amino acid sequence of the junction bridges between variant exon V6 and constant exon C6. "CD44V6 product" also includes homologues (see below) of said amino acid sequence in which one or more amino acids have been added, deleted, substituted (see below) or chemically modified (see below), as well as fragments (see below) of this sequence having at least 6 amino acids.

As referred to herein, the term "CD44V7 product", interchangeably referred to also as "CD44V7 protein" or "CD44V7 peptide" is a polypeptide having an amino acid sequence encoded by the CD44V7 coding sequence. By "polypeptide" is intended a peptide or protein, as well as peptides or proteins having chemically modified amino acids (see below) such as a glycopeptide or glycoprotein. The amino acid sequence of CD44V7 product is shown in SEQ ID NO: 6. The amino acid sequence of the C5-V7-C6 region of CD44V7 corresponds to coordinates 214-276 in SEQ ID NO: 6. FIG. 4A lists the amino acid sequence of variant exon V7. FIG. 4B lists the amino acid sequence of the junction bridges between constant exon C5 and variant exon V7. FIG. 4C lists the amino acid sequence of the junction bridges between variant exon V7 and constant exon C6. "CD44V10 product" also includes homologues (see below) of said amino acid sequence in which one or more amino acids have been added, deleted, substituted (see below) or chemically modified (see below) as well as fragments (see below) of this sequence having at least 6 amino acids.

As referred to herein, the term "CD44V10 product", interchangeably referred to also as "CD44V10 protein" or "CD44V10 peptide" is a polypeptide having an amino acid sequence encoded by the CD44V10 coding sequence. By "polypeptide" is intended a peptide or protein, as well as peptides or proteins having chemically modified amino acids (see below) such as a glycopeptide or glycoprotein. The amino acid sequence of CD44V10 product is shown in SEQ ID NO: 8. The amino acid sequence of the C5-V10-C6 region of CD44V10 corresponds to coordinates 214-300 in SEQ ID NO: 8. FIG. 5A lists the amino acid sequence of variant exon V10. FIG. 5B lists the amino acid sequence of the junction bridges between constant exon C5 and variant exon V10. FIG. 5C lists the amino acid sequence of the junction bridges between variant exon V10 and constant exon C6. "CD44V10 product" also includes homologues (see below) of said amino acid sequence in which one or more amino acids have been added, deleted, substituted (see below) or chemically modified (see below) as well as fragments (see below) of this sequence having at least 6 amino acids.

Homologue relates to polypeptide having an amino acid sequence, that is at least 90% identical to the sequence of any one of SEQ ID NO: 2, SEQ ID NO: 4, SEQ ID NO: 6, SEQ ID NO: 8 or at least 90% identical to a fragment of at least 6 amino acids of any one of the sequence of SEQ ID NO: 2, SEQ ID NO: 4, SEQ ID NO: 6, SEQ ID NO: 8. The variation in amino acid sequence between the homologue and the sequence of any one of SEQ ID NO: 2, SEQ ID NO: 4, SEQ ID NO: 6, SEQ ID NO: 8 or a fragment thereof, arises from the addition, deletion, substitution or chemical modification of one or more amino acids of the sequence of any one of SEQ ID NO: 2, SEQ ID NO: 4, SEQ ID NO: 6, SEQ ID NO: 8.

Where the homologue contains a substitution, the substitution is preferably a conservative one.

"Nucleic acid molecule" or "nucleic acid" or "polynucleotide" relates to a single-stranded or double-stranded polymer composed of DNA (Deoxyribonucleic acid) nucleotides, RNA (Ribonucleic acid) nucleotides or a combination of both types, and may include natural nucleotides, chemically modified nucleotides and synthetic nucleotides.

"Amino acid sequence" relates to a sequence composed of any one of the 20 naturally occurring amino acids, amino acids that have been chemically modified (see below), or synthetic amino acids.

"Conservative substitution" refers to the substitution of an amino acid in one class by an amino acid of the same class, where a class is defined by common physico-chemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gin, Glu); Class IV (His, Arg, Lys); Class V (He, Leu, Val, Met); and Class VI (Phe, Tyr, Tip). For example, substitution of an Asp for another Class III residue such as Asn, Gin, or Glu, is a conservative substitution.

"Non-conservative substitution"—refers to the substitution of an amino acid in one class with an amino acid from another class; for example, substitution of an Ala, a Class II residue, with a Class III residue such as Asp, Asn, Glu, or Gin.

"Chemically modified" refers to a product (protein) where at least one of its amino acid residues is modified either by natural processes, such as processing or other posttranslational modifications, or by chemical modification techniques which are well known in the art. Among the numerous known modifications, typical, but not exclusive, examples include: acetylation, acylation, amidation, ADP-ribosylation, glycosylation, glycosaminoglycanation, GPI anchor formation, covalent attachment of a lipid or lipid derivative, methylation, myristlyation, pegylation, prenylation, phos-phorylation, ubiqutination, or any similar process.

"Optimal alignment" is defined as an alignment giving the highest percent identity score. Such alignment can be performed using a variety of commercially available sequence analysis programs, such as the local alignment program LALIGN, using a setup of default parameters.

"Having at least 90% identity" with respect to two sets of amino acid or nucleic acid sequences, refers to the percentage of residues that are identical in the two sequences when the sequences are optimally aligned. Thus, at least 90% amino acid sequence identity means that at least 90% of the amino acids in two or more optimally aligned polypeptide sequences are identical; however this definition explicitly excludes sequences which are 100% identical with the original nucleic acid sequence or original protein sequence from which variant was varied.

"Isolated nucleic acid molecule having a variant nucleic acid sequence" and "isolated polynucleotide molecule" refers to a nucleic acid molecule that comprises the variant coding sequence. The isolated nucleic acid molecule may include, but is not limited to, the variant coding sequence as an independent insert; may include the variant coding sequence fused to an additional coding sequence, encoding together a fusion protein in which the variant coding sequence is the dominant coding sequence (for example, the additional coding sequence may code for a signal peptide); the variant coding sequence may be in combination with non-coding sequences, for example introns or control elements, such as promoter and terminator elements or 5' and/or 3' untranslated regions, effective for expression of the coding sequence in a suitable host; or may be a vector in which the variant protein coding sequence is heterologous.

"Expression vector" refers to vectors that have the ability to incorporate and express heterologous DNA fragments in a foreign cell. Many prokaryotic and eukaryotic expression vectors are known and/or commercially available. Selection of appropriate expression vectors is within the knowledge of those having skill in the art.

"Oligonucleotide" refers to a single-stranded or double-stranded oligomer or polymer of ribo-nucleic acid (RNA) or deoxyribonucleic acid (DNA) or mimetics thereof. This term includes oligonucleotides composed of naturally occurring bases, sugars, and covalent internucleoside linkages (for example, backbone), as well as oligonucleotides having non-naturally occurring portions, which function similarly to respective naturally occurring portions.

"Deletion" refers to a change in either nucleotide or amino acid sequence in which one or more nucleotides or amino acid residues, respectively, are absent as compared to the naturally occurring sequence.

"Insertion" or "addition" refers to that change in a nucleotide or amino acid sequence, which has resulted in the addition of one or more nucleotides or amino acid residues, respectively, as compared to the naturally occurring sequence.

"Substitution" refers to replacement of one or more nucleotides or amino acids by different nucleotides or amino acids, respectively, as compared to the naturally occurring sequence. Regarding amino acid sequences, the substitution may be conservative or non-conservative.

"Antibody" refers to antibodies of any of the classes IgG, IgM, IgD, IgA, and IgE antibody. The definition includes polyclonal antibodies or monoclonal antibodies. This term refers to whole antibodies or fragments of the antibodies comprising the antigen-binding domain of the anti-variant product antibodies, for example scFv, Fab, F(ab')2, other antibodies without the Fc portion, single chain antibodies, bispecific antibodies, diabodies, other fragments consisting of essentially only the variable, antigen-binding domain of the antibody, and the like, which substantially retain the antigen-binding characteristics of the whole antibody from which they were derived.

"Agonist" refers to a molecule that mimics the effect of the CD44 variant product or has enhanced activity compared with the CD44 variant product, or at times even increases or prolongs the duration of the biological activity of the variant product, as compared to that induced by the variant product itself. The mechanism may be by any mechanism known to prolonging activities of biological molecules such as binding to receptors; prolonging the lifetime of the molecules; increasing the activity of the molecules on its target; increasing the affinity of molecules to its receptor; inhibiting degradation or proteolysis of the molecules, and so forth. Agonists may be polypeptides, nucleic acids, carbohydrates, lipids, or derivatives thereof, or any other molecules, which can positively modulate the activity of the variant product.

"Antagonist" refers to a molecule that inhibits or shortens the duration of the biological activity of the CD44 variant product. This may be achieved by any mechanism known to deactivate or inhibit biological molecules such as blocking of the receptor, blocking of an active site, competition on a binding site, enhancement of degradation, and the like. Antagonists may be polypeptides, nucleic acids, carbohydrates, lipids, or derivatives thereof, or any other molecules, which can negatively modulate the activity of the CD44 variant product.

"Biological sample"—The biological sample used in various embodiments and examples can be any appropriate body-derived sample. The sample may include fluid samples such as whole blood, peripheral blood monocytes, leukocytes. The samples may include various cells and tissues. The sample may include fixed and/or embedded tissue sections. The samples may be either freshly extracted or frozen. The samples may be obtained from living or dead subjects and may be obtained from any organism, such as, for example, humans, mice and rats.

"Treating a disease" refers to administering a composition, which includes at least one reagent/substance, effective to ameliorate symptoms associated with a disease, to lessen the severity or cure the disease, or to prevent the disease from occurring.

As referred to herein, the term "modulate" is directed to affecting (changing) the expression and/or activity of a nucleic acid and/or a polypeptide. The term modulating may refer to increasing and/or attenuating (downregulating) the expression and/or activity of the nucleic acid and/or the polypeptide.

"Detection, "Diagnosis" refer to methods of detection of a disease, symptom, disorder, pathological or normal condition; classifying a disease, symptom, disorder, pathological condition; determining a severity of a disease, symptom, disorder, pathological condition; monitoring disease, symptom, disorder, pathological condition progression; forecasting an outcome and/or prospects of recovery thereof.

"Probe"—a nucleic acid molecule comprising the variant coding sequence, or a sequence complementary therewith, when used to detect the presence of other similar sequences in a sample. The detection is carried out by identification of hybridization complexes between the probe and the assayed sequence. The probe, in some embodiments, may be attached to a solid support or to a detectable label. The probe will generally be single stranded and will generally be between 10 and 100 nucleotides. The particular properties of a probe will depend upon the particular use and are readily within the competence of one of ordinary skill in the art to determine.

"Primer pair"—a set of two nucleic acid molecules ("primers"), each of which can serve to prime template-directed polymerization by a polymerase or transcriptase, which primers hybridize to the opposite strands of a double stranded nucleic acid sequence ("template") in such manner as to direct the polymerization (and amplification) of the double-stranded sequence nucleotide sequence located between regions of primer hybridization. Such a primer pair can be used in the well-known polymerase chain reaction (PCR). The design of primer pairs is well known in the art and will depend upon the particular sequence to be amplified. In general, the primers are single-stranded, between 10 and 40 bases in length and hybridize to regions of the template sequence located between 50 and 2000 bases apart.

"Splice junction", interchangeably referred to as "bridging junction" relates to the nucleotide region wherein splicing occurs. This is the region where an exon connects to its flanking exons, in the sequence of the processed transcript.

"Hybridization", or "nucleic acid hybridization" relates to the process of combining (interacting) between a single-stranded nucleic acid molecule and a complimentary nucleic acid molecule into one molecule.

Reference is now made to FIG. 1, which schematically illustrates the human CD44 gene structure. FIG. 1A illustrates the structure of the human CD44 gene, which is composed of 9 variable exons (filled squares, marked V2-10) and constant exons (empty squares, marked as C1-5 and C6-10). FIG. 1B schematically illustrates the structure of the CD44 variant transcript CD44V3, which includes, in addition to the constant exons, variable exon 3. FIG. 1C schematically illustrates the structure of the CD44 variant transcript CD44V6, which includes, in addition to the constant exons, variable exon 6. FIG. 1D schematically illustrates the structure of the CD44 variant transcript CD44V7, which includes, in addition to the constant exons, variable exon 7. FIG. 1E schematically illustrates the structure of the CD44 variant transcript CD44V10, which includes, in addition to the constant exons, variable exon 10.

According to some embodiments, RNA samples may be extracted from biological samples of subjects diagnosed with neurodegenerative disease (patients) or from model animals, such as, for example, transgenic mice, which are used as models of neurodegenerative diseases. The extracted RNA may include total RNA or mRNA. The extracted RNA may be reverse transcribed and used in a PCR amplification reaction. The PCR amplification reaction may further include primers whose nucleotide sequence may be derived from regions within various variant exons of a CD44 gene, regions within various constant exons of a CD44 gene, regions that encompass nucleotide sequence of junctions regions bridging constant and variable exons, or any combination thereof. The resulting PCR products may then be analyzed and their sequence determined. In this manner, various CD44 transcripts may be identified that may include, among others, novel CD44 splice variant transcripts that were not previously described in the art.

Furthermore, RNA samples may be extracted from biological samples of subjects diagnosed with neurodegenerative disease (patients) as well as from age and sex matching subjects that were not diagnosed with a neurodegenerative disease (normal control). The extracted RNA may include total RNA or mRNA. The extracted RNA may be reverse transcribed and used in a PCR amplification reaction. The PCR amplification reaction may further include primers whose nucleotide sequence may be derived from regions within various variant exons of a CD44 gene, regions within various constant exons of a CD44 gene, regions that encompass nucleotide sequence of junction regions that bridge between constant and variable exons, and any combination thereof. The resulting PCR products obtained from the patient biological samples and the normal control subjects may then be analyzed and their sequence may be determined. The PCR products may include CD44 transcripts that may include, among others, novel CD44 splice variant transcripts that were not previously described in the art. Furthermore, level of expression of the various PCR products, which represent various CD44 variant transcripts, may be compared between samples obtained from patients and samples obtained from normal controls. Level of expression of the various CD44 variant transcripts and comparison of the level of expression between different samples may be determined by various methods which are known in the art, such as, for example, by the method of semi quantitative Reverse Transcription (RT)-PCR, Real Time PCR, and the like. For example, such comparison may indicate exclusive expression of specific splice variant(s) in samples obtained from patients as compared to samples obtained from normal controls. For example, such comparison may indicate an elevated level of expression (up regulation) of specific splice variant(s) in samples obtained from patients as compared to samples obtained from normal controls. For example, such comparison may indicate a decrease in level of expression (down-regulation) of specific splice variant(s) in samples obtained from patients as compared to samples obtained from normal controls. For example, such comparison may indicate that no change is observed in level of expression of specific splice variant(s) in samples obtained from patients as compared to samples obtained from normal controls. For example, such comparison may indicate exclusive expression of specific splice variant(s) in samples obtained from normal controls as compared to samples obtained from patients.

In accordance with some exemplary embodiments, total RNA is extracted from post-mortem hippocampus samples from subjects diagnosed with Alzheimer disease (AD patients) as well as from age and sex matching subjects that were not diagnosed with the disease (normal control). The RNA is reverse transcribed and used in a PCR amplification reaction, as further detailed in Example 1, hereinbelow. The PCR further include primers whose nucleotide sequence may be derived from regions within various variant exons of a CD44 gene, regions within various constant exons of a CD44 gene, regions that encompass nucleotide sequence of junctions regions bridging constant and variable exons, and any combination thereof. Exemplary primer sequences are listed in Example 1, hereinbelow. Analysis of the resulting PCR products thus obtained indicate several splice variants of CD44, whose expression is upregulated in samples obtained from patients as compared to samples obtained from normal controls. In particular, several CD44 splice variants were thus identified, which contained a single non-skipped variant exon flanked by the constant exons of CD44, and exhibited a significantly increased expression in AD patients as compared to normal controls. The CD44 splice variants thus identified include CD44V3, CD44V6, CD44V7 and CD44V10. Real-time PCR experiments, detailed in Example 2 hereinbelow, show that the CD44V3, CD44V6, and CD44V10 splice variants exhibited about 7.17, 7.02 and 18.15-fold upregulation of expression in AD patients as compared to normal control, respectively. In addition, the CD44S isoform of CD44 exhibited about 4.95 upregulation of expression in AD patients as compared to normal control.

In accordance with additional embodiments, total RNA is extracted from APP751 transgenic mice, which may be used as a model for AD-like pathology, as further detailed in Example 3 hereinbelow. RNA from hippocampal tissues is isolated from 7-7.5 months old female $APP_{751}$ transgenic mice and non-transgenic litter mates. The RNA is reverse transcribed and used in PCR amplification reaction, as further detailed in Example 3, hereinbelow. The results indicated a 7.2 fold increase in expression of mRNA encoding a transcript having the V7-C10 junction in $APP_{751}$ transgenic mice compared to the control non-transgenic mice. Under identical conditions, the expression levels of CD44S exhibited a 16% increase. The up regulation of CD44V7 expression in APP751 transgenic mice (as demonstrated in Example 3), along with the finding of CD44V7 in brains of AD patients (as demonstrated in Example 1), indicate the involvement of CD44V7 in AD pathology, for example, downstream of accumulation of Aβ, the accumulation of which in specific brain region is one of the hallmarks of AD.

According to some embodiments, and as schematically illustrated in FIG. 1B, splice variant CD44V3 transcript includes at least constant exon C5, variant exon V3 and constant exon C6. More preferably, splice variant CD44V3 transcript includes constant exons C1-C5, variant exon 3 and constant exons C6-C9. A Blast search on public databases of human expressed sequences using default parameters, and using the nucleotide sequence of CD44V3 resulted in a single EST (accession number DA283531) with no identity to any known mRNA. A similar Blast search using the nucleotide sequence of the C5-V3-C6 region of CD44V3 (coordinates 639-822 in SEQ ID NO: 1 and as illustrated in FIG. 2A-C) resulted in similar results.

According to some embodiments, and as schematically illustrated in FIG. 1C, splice variant CD44V6 transcripts includes at least constant exon C5, variant exon V6 and constant exon C6. More preferably, splice variant CD44V6 transcript includes constant exons C1-C5, variant exon 6 and constant exons C6-C9. A Blast search on public databases of human expressed sequences using default parameters, and using the nucleotide sequence of CD44V6 did not result in any similar EST or mRNA sequences. A similar Blast search using the nucleotide sequence of the C5-V6-C6 region of CD44V6 (coordinates 639-825 in SEQ ID NO: 3 and as illustrated in FIG. 3A-C) have shown that no mRNAs or EST were found to contain a combination of nucleotide sequence of both C5V6 and V6C6 in the same molecule. Thus, CD44V6 is a novel splice variant of the CD44 gene, which has not been previously described. Guriec et al. (Breast Cancer Res Treat. 1997 44:261-8) mention V6 alone but only checked the V6-C6 region and no other region connected to V6.

According to some embodiments, and as schematically illustrated in FIG. 1D, splice variant CD44V7 transcripts includes at least constant exon C5, variant exon V7 and constant exon C6. More preferably, splice variant CD44V7 transcript includes constant exons C1-C5, variant exon 7 and constant exons C6-C9. The nucleotide sequence of the C5-V7-C6 region of CD44V7 corresponds to coordinates 639-828 in SEQ ID NO: 5. A Blast search on public databases of human expressed sequences using default parameters, and using the nucleotide sequence of CD44V7 did not result in any identical EST or mRNA sequences, that is, an mRNA which contain both C5V7 and V7C6 bridges on the same molecule was not found.

According to some embodiments, and as schematically illustrated in FIG. 1E, splice variant CD44V10 transcripts includes at least constant exon C5, variant exon V10 and constant exon C6. More preferably, splice variant CD44V10 transcript includes constant exons C1-C5, variant exon 10 and constant exons C6-C9. A Blast search on public databases of human expressed sequences using default parameters, and using the nucleotide sequence of CD44V10 resulted in one mRNA (EF581837) and two ESTs (CD641177 and AW995521). A similar Blast search using the nucleotide sequence of the C5-V10-C6 region of CD44V10 (coordinates 639-900 in SEQ ID NO: 7 and as illustrated in FIG. 5A-C resulted in similar results.

According to further exemplary embodiments, and as further detailed in Example 4, hereinbelow, total RNA is extracted from post-mortem lumbar cord and motor cortex samples from subjects diagnosed with ALS (ALS patients) as well as from subjects that were not diagnosed with the disease (normal control). The RNA is reverse transcribed and used in a PCR amplification reaction. The PCR further include primers whose nucleotide sequence may be derived from regions within various variant exons of a CD44 gene, regions within various constant exons of a CD44 gene, regions that encompass nucleotide sequence of junctions regions bridging constant and variable exons, and any combination thereof. Analysis of the resulting PCR products thus obtained indicated several splice variants of CD44, whose expression was upregulated in samples obtained from patients as compared to samples obtained from normal controls. In particular, several CD44 splice variants were identified, which contained a single non-skipped variant exon flanked by the constant exons of CD44, and exhibited a significantly increased expression in AD patients as compared to normal controls. The CD44 splice variants thus identified include CD44V3, CD44V6 and CD44V10.

The CD44 variant transcripts thus identified, such as, for example, CD44V3, CD44V6, CD44V7 and CD44V10, and their respective protein products may be involved in inflammatory processes which could be mediated by resident glial cells (microglia or astrocytes) or by infiltrating inflammatory cells such as T lymphocytes that could be either protective or detrimental and are stimulated in the course of the diseases into the non-skipping of some exons. The selection of splice variants appears to be species and diseases specific.

According to some embodiments, peptides derived from the sequences of various CD44 variant proteins may be prepared by various means, such as, for example, by chemical synthesis and/or recombinant methods and used as antigens for the production of specific antibodies directed against those peptides. The antibodies thus prepared may include polyclonal and monoclonal antibodies and may specifically recognize the various CD44 variant proteins. The preparation and purification of the antibodies may be performed by any method known in the art. The antibodies that specifically recognize and bind the various CD44 variant proteins exhibit at least 2-fold higher affinity as compared to binding to other CD44 variant proteins known in the art, which are not described in any of the embodiments described herein. Specificity of the binding may be evaluated by various methods that are well known to those skilled in the art, such as binding assays, biological assays and any combination thereof.

According to some embodiments, peptides derived from the sequences of various CD44 variant products identified herein, such as CD44V3 product, CD44V6 product, CD44V7 product, CD44S product and CD44V10 product, may be synthesized chemically by solid phase synthesis (Merrifield, J. 1964, Biochemistry, 3:1385-90) and used for the production of antibodies that may specifically recognize the CD44 variant proteins. The antibodies may include, for example, polyclonal antibodies and/or monoclonal antibodies. Preferably, the peptides derived from the sequences of the various CD44 variant products may be obtained from regions that correspond to the junctions between the variable exons and the constant exons. A peptide derived from the CD44V3 protein may include, for example, the junction region which corresponds to amino acid sequence bridging exons C5 and V3 (Amino acids 214-233 in SEQ ID NO: 2 and FIG. 2B). For example, a peptide derived from the CD44V3 protein may include the junction region, which corresponds to amino acid sequence bridging exons V3 and C6 (Amino acids 256-275 in SEQ ID NO: 2 and as illustrated in FIG. 2C). A peptide derived from the CD44V6 protein may include, for example, the junction region which corresponds to amino acid sequence bridging exons C5 and V6 (Amino acids 214-233 in SEQ ID NO: 4 and FIG. 3B). For example, a peptide derived from the CD44V6 protein may include the junction region which corresponds to amino acid sequence bridging exons V6 and C6 (Amino acids 257-276 in SEQ ID NO: 4 and as illustrated in FIG. 3C). A peptide derived from the CD44V10 protein may include, for example, the junction region which corresponds to amino acid sequence bridging exons C5 and V10 (Amino acids 214-233 in SEQ ID NO: 8 and FIG. 5B). For example, a peptide derived from the CD44V10 protein may include the junction region which corresponds to amino acid sequence bridging exons V10 and C6 (Amino acids 282-301 in SEQ ID NO: 8 and as illustrated in FIG. 5C). Splenocytes of mice immunized with these peptides may be fused to myeloma cells, and hybridomas producing specific monoclonal Abs may be selected by testing the ability of supernatants of these cells to bind to Namalwa Burkitt's lymphoma cell lines stably transfected with recombinant constructs encoding CD44 variants but not to non-transfected or CD44s-transfected control cells.

According to some embodiments, reagents, such as specific antibodies, which may specifically react against and recognize various CD44 splice variant proteins, may be used in the diagnosis of neurodegenerative diseases. Analysis of the expression of the various CD44 splice variant proteins may be performed on various biological samples obtained from individuals to be tested. Such samples may include, for example, plasma samples, tissue samples and the like. Analysis of the samples may be used to determine the presence, existence, as well as level of expression of the various CD44 variant proteins. The analysis may include various well known methods used to determine protein expression in a sample, such as Western blotting, Enzyme Linked Immunosorbent Assay (ELISA), Radio Immuno Assay (RIA), and the like. Presence and/or level of expression of the CD44 variant proteins may be compared to a known, pre-calibrated control, and the difference in expression between the tested individuals and the control may give an indication as to the existence of a disease as well as to the level of progression of the disease.

Figure 6:
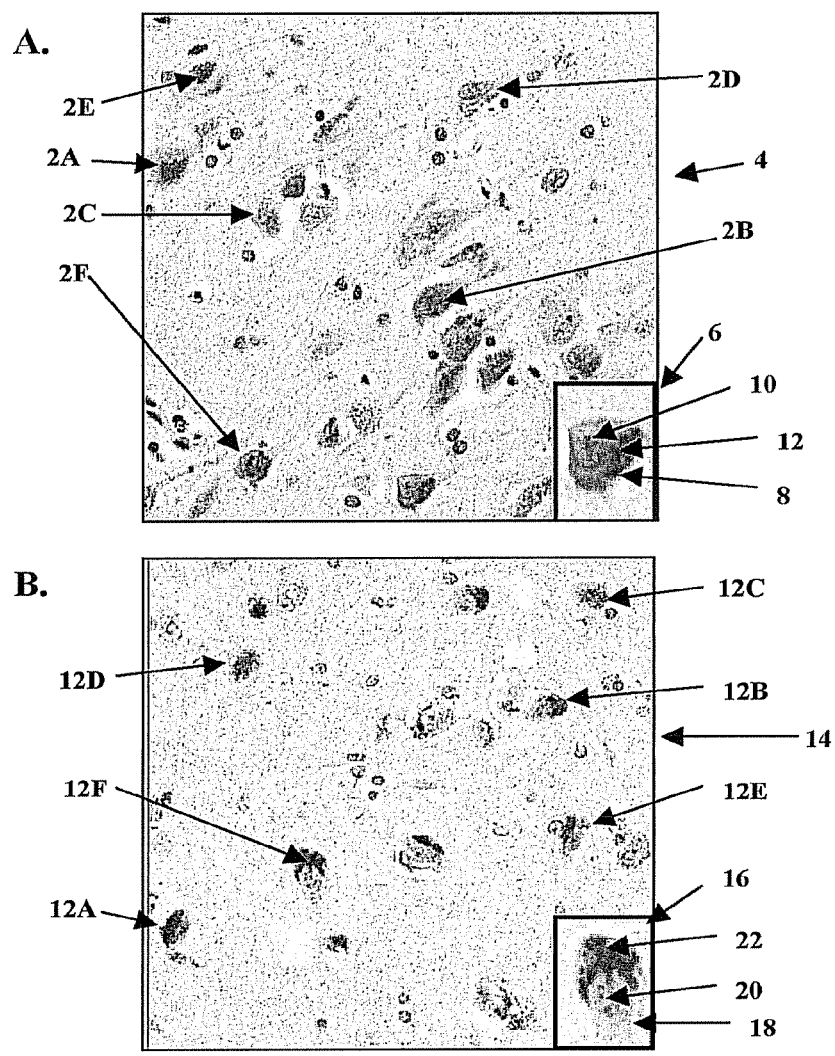
FIG. 6 demonstrates immunohistochemical staining of hippocampal section of an AD patient with CD44V6 antibody.

In accordance with some exemplary embodiments, immunohistochemical analysis of hippocampal tissues of AD patients' brains is performed, as further detailed in Example 5, hereinbelow. Specific antibodies against CD44S, CD44V3, CD44V6 or CD44V10 for immunohistochemical staining of the AD patients' brain tissue. The immunohistochemistry staining results demonstrate differential cellular and subcellular localizations of the various CD44 isoforms. Whereas the CD44S is found mainly in astrocytes and within senile plaques, CD44V6 and CD44V10 staining is found in neurons in paranuclear areas that overlap region of lipofuscsin autofluorescence, as detailed in Example 5. CD44V3 staining was found in both astrocytes and neuronal paranuclear areas. Lipofuscin is a lysosomal complex of oxidized protein and lipid degradation residues, which is accumulated in aged neurons. The results demonstrate that in contrast to CD44S, CD44 variant proteins, which are expressed in neurons, may have a direct role in the pathophysiological process that may lead to neuronal cell death. For example, CD44 variants may have a novel function in intracellular processing of Aβ from the APP precursor protein in neurons. For example, CD44 variants such as CD44V3, CD44V6, CD44V7 and CD44V10 may be involved in autophagy, the major pathway involved in degradation of long-lived proteins and organelles, cellular remodeling, and survival during nutrient starvation. Autophagy is involved in the intracellular degradation of aggregation-prone α-synuclein (Ravikumar Nat. Genet. 2004, 36: 585-95) and huntingtin (Shibata J. Biol. Chem. 2006, 281: 14474-85). Autophagic vacuoles have previously been identified in dystrophic neurites in AD brains and may be a site for Aβ production (Yu et at J. Cell Biol. 2005, 171: 87-98). Autophagy was recently shown to have an important preventive role in the Aβ accumulation, extracellular Aβ deposition and neuron degeneration in AD mice model (Pickford et al J Clin Invest. 2008, 118: 2190-99). Reference is now made to FIG. 6A and FIG. 6B, which illustrates typical staining of hippocampal section of AD patient with CD44V6 and CD44V10 antibodies, respectively. As shown in FIG. 6A, various neuronal cells, such as, for example, neuronal cells 2A-F may be identified within hippocampal section (4). The cells may be stained, such as exemplified by cell 2F, which is a typical positively stained neuron. The lower right hand side of FIG. 6A (panel 6), shows a magnified view of an exemplary positively stained cell (8), wherein the cell nucleus (10) is not stained, while the paranuclear and cytoplasm compartments (12), are positively stained with a CD44V6 antibody, that is, the CD44V6 product is expressed is these cell compartments. As shown in FIG. 6B, various neuronal cells, such as, for example, neuronal cells 12A-F may be identified within hippocampal section (14). The cells may be stained, such as exemplified by cell 12F, which is a typical positively stained neuron. The lower right hand side of FIG. 6B (panel 16), shows a magnified view of an exemplary positively stained cell (18), wherein the cell nucleus (20) is not stained, while the paranuclear and cytoplasm compartments (22), are positively stained with a CD44V10 antibody, that is, the CD44V10 product is expressed is these cell compartments. Altogether, the staining results show strong staining in neuronal cytoplasm, and hence this is the neuronal compartment werein the CD44 variant products are expressed.

According to some embodiments, there is thus provided a qualitative method of diagnosing the presence and/or progression level of a neurodegenerative disease, such as, for example, AD and ALS. The method may include the use of reagents that may specifically react against and recognize the various CD44 splice variant proteins, such as CD44V3 protein, CD44V6 protein, CD44V10 protein, or any combination thereof. The reagents may include, for example specific monoclonal and/or polyclonal antibodies, which individually recognize the various CD44 variant proteins. The presence of the CD44 variant proteins, such as CD44V3 protein, CD44V6 protein and/or CD44V10 protein may be tested in a biological sample obtained from a tested subject, such as, for example, a tissue, a fluid sample, cell, and the like. The presence of the CD44 splice variant proteins, such as CD44V3 protein, CD44V6 protein and/or CD44V10 protein may be tested by immunohistochemistry and/or Western Blot analysis performed on tissue sections and/or protein extracts obtained from the biological samples. As demonstrated above, detected expression (presence) of the various CD44 splice variant proteins, such as CD44V3 protein, CD44V6 protein, CD44V10 protein, or any combination thereof, may be indicative of a presence of a neurodegenerative disease in the tested subject. Moreover, the method as described herein as a qualitative method may also be used as a quantitative method. In the quantitative method, the level of expression of the CD44V3 protein, CD44V6 protein, CD44V10 protein or any combination thereof in the tested subject is compared to a known calibrated level of expression of these proteins. By quantization of the level of expression of the CD44 splice variant proteins, such as CD44V3 protein, CD44V6 protein, CD44V10 protein, the progression state of the neurodegenerative disease may be deduced.

According to some embodiments, reagents, such as specific antibodies, which may specifically react against and recognize various CD44 splice variants proteins, may be used for the treatment of neurodegenerative diseases, for their onset or progression. There is therefore provided a method for treating a neurodegenerative disease in a patient in need, including administering to a patient in need an effective amount of a reagent, such as a specific antibody directed against a CD44 splice variant protein, such as a CD44V3 protein, CD44V6 protein, CD44V10 protein, or any combination thereof. The reagent, such as a specific antibody, may downregulate the activity or expression of the CD44 splice variants, thereby treating the neurodegenerative disease.

According to some embodiments, there are provided oligonucleotide molecules that may be used for identification, characterization, detection and quantitation of the expression of the CD44V3, CD44V6, CD44V7 and CD44V10 splice variants in various biological samples. The oligonucleotide molecules may include DNA or RNA nucleic acids such as, for example, oligonucleotide probes, oligonucleotide primers or any combination thereof, whose nucleotide sequence may hybridize to at least a region of the nucleotide sequence of the CD44V3 (SEQ ID NO: 1) and/or CD44V6 (SEQ ID NO: 3) and/or CD44V7 (SEQ ID NO: 5) and/or CD44V10 (SEQ ID NO: 7) transcripts. For example, the oligonucleotide molecules may include a nucleic acid probe. A suitable nucleic acid probe may include 100-200 nucleotides, and such a probe may be used to identify and quantitate expression of CD44 splice variants in various biological systems. Use of the probe for identification and quantitation of expression of the CD44 splice variant may be achieved by various methods that rely on specific hybridization of the probe with the CD44 splice variants. Such methods may include, for example, Northern blot analysis and RNA in-situ hybridization. For example, the nucleic acid molecules may also include primer pairs. Primer pairs are two short oligonucleotide molecules (such as, for example, in the length of 10-30 nucleotides) that may be used to detect and quantitate expression of the mRNA of the various CD44 splice variants (CD44 splice variant transcripts) in such method as Reverse Transcriptase Polymerase Chain Reaction (RT-PCR) that is well known in the art. In this method, RNA molecules extracted from a biological sample are reverse transcribed to DNA by a reverse transcriptase enzyme. The resulting DNA molecule is then used as a template in a PCR reaction along with the specific primer pairs, whose sequence is identical or complementary to at least part of the region of the individual CD44 splice variants. If a specific CD44 splice variant is expressed (meaning that its mRNA is found in a biological sample), upon the amplification reaction, a PCR product may be observed and its level may be quantitated. For each of the various CD44 splice variants described hereinabove, at least one specific primer pair may be designed and prepared. The sequence of the primer pairs may preferably be derived from the unique sequence regions of each of the splice variants. The unique sequence regions of each of the splice variants are most preferably at close proximity to the junction regions bridging the constant and the variant exons (splice junction). Exemplary specific primer pairs sequences that may be used for that purpose are listed in Examples 1 and 3, hereinbelow.

According to some embodiments, oligonucleotides, such as specific probes and primer pairs, such as those listed in Examples 1 and 3, hereinbelow, which may specifically recognize various CD44 splice variants, may thus be used for the diagnosis of neurodegenerative diseases. Analysis of the expression of the various CD44 splice variant may be performed on various biological samples obtained from individuals to be tested. Such samples may include, for example, plasma samples, tissue samples and the like. Analysis of the samples may be used to determine the presence, existence, as well as level of expression of the various CD44 variants. The analysis may include various well-known methods used to determine transcript expression in a sample, such as RT-PCR, RT-Real-Time PCR, Northern blot, In-situ hybridization, and the like. Presence and/or level of expression of the CD44 variant transcripts may be compared to a known, pre-calibrated control, and the difference in expression between the tested individuals and the control may give an indication as to the existence of a disease, as well as to the level of progression of the disease. For example, as detailed above and in Examples 1-2, expression levels of various CD44 transcripts, such as, for example, CD44S, CD44V3, CD44V6 and/or CD44V10 is significantly elevated in AD patients' brains as compared to control brains. For example, CD44V3 and CD44V6 transcript expression is increased by about 7 fold in AD patients, as compared to control. For example, CD44V10 expression is increased by about 18 fold in AD patients, as compared to control.

According to some embodiments, there is thus further provided a method of diagnosing or monitoring a neurodegenerative disease (such as, ALS, AD, PD) in a patient, which includes detecting the expression level of a nucleic acid in a biological sample of the patient, wherein said nucleic acid comprises: SEQ ID NO: 1, SEQ ID NO: 3, SEQ ID NO: 5, SEQ ID NO: 7, or any combination thereof. The biological sample may include a cell, a tissue, a biological fluid, or any combination thereof. The expression level may be detected by determining the expression levels of RNA encoded by the nucleic acid, which is isolated from the biological sample. Detection of the RNA expression levels may include various methods, such as, for example, PCR, RT-PCR, Northern blot, Real-time PCR, and the like, or any combination thereof that may be used to detect hybridization of the RNA to an oligonucleotide, such as, for example, DNA, RNA, cDNA, genomic DNA, synthetic oligonucleotides, and the like, or any combination thereof. For example, the method of diagnosing may include detecting the expression level of a polypeptide in a biological sample of the patient, wherein the polypeptide may be selected from a group that includes: SEQ ID NO: 2, SEQ ID NO: 4, SEQ ID NO: 6, SEQ ID NO: 8, or any combination thereof. Detecting the expression level of the polypeptide may include detecting immuno-complexes of the polypeptide and an antibody adapted to specifically bind the polypeptide, by such methods as, but not limited to: Western Blot, immunohistochemistry, immunocytochemistry, enzyme linked immunosorbent assay (ELISA), and the like, or any combination thereof. For example, a qualitative method of diagnosing the presence and/or progression level of a neurodegenerative disease, such as, for example, AD, ALS and Parkinson disease, may include the use of oligonucleotides that recognize the various CD44 splice variants transcripts, such as, for example, CD44S transcript, CD44V3 transcript, CD44V6 transcript, CD44V7 transcript CD44V10 transcript, or any combination thereof. The oligonucleotides may include, for example, synthetic oligonucleotides, such as, for example, primer pairs, such as those listed in Examples 1 and 3. The presence of the CD44 variant transcripts, such as CD44V3 transcript, CD44V6 transcript, CD44V7 transcript, CD44S transcript, and/or CD44V10 transcript may be tested in a biological sample obtained from a tested subject. The presence of the CD44 splice variant transcript, such as CD44V3 transcript, CD44V6 transcript, CD44V7 transcript, CD44V10 transcript or any combination thereof, may be tested by, for example, RT-PCR analysis, RT-Real-Time PCR analysis, and the like, performed on RNA extracts obtained from the biological samples. Detected expression (presence) of the various CD44 splice variant transcripts, such as, for example, CD44V3 transcript, CD44V6 transcript, CD44V10 transcript, CD44S, CD44V7, or any combination thereof, may be indicative of a presence of a neurodegenerative disease in the tested subject. Moreover, the method as described herein as a qualitative method may also be used as a quantitative method. In the quantitative method, the level of expression of the CD44V3 transcript, CD44V6 transcript, CD44V6 transcript, CD44V10 transcript, CD44S, or any combination thereof, in the tested subject, may be determined, for example by RT-PCR, method, or Real-Time PCR method, and is compared to a known calibrated level of expression of these transcripts. By quantization of the level of expression of the CD44 splice variant transcripts, such as CD44V3 transcript and/or CD44V6 transcript, CD44V6 transcript, and/or CD44V10 transcript, and/or CD44S transcript, the progression state of the neurodegenerative disease may be deduced.

Figure 7:
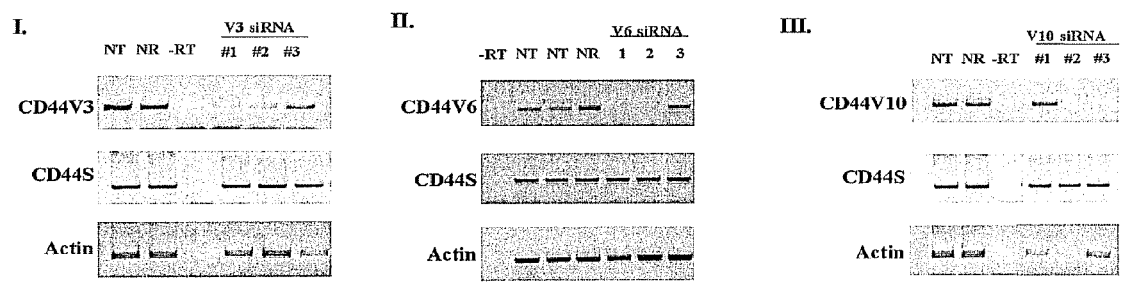
FIG. 7 demonstrates siRNA effect on mRNA expression of various CD44 variants, according to some embodiments.

According to some embodiments, various methods, reagents and techniques that are known in the art may be used to affect the expression level of the various CD44 variant transcripts, CD44V3, CD44V6 and/or CD44V10. For example, these techniques may include, among others, the use of nucleic acid molecules (usually in the form of oligonucleotides) which may have at least in part a complementary sequence to that of the CD44 variant transcripts, CD44V3, CD44V6 and/or CD44V10. Such nucleic acid molecules may include, for example, small interference RNA (siRNA), antisense oligonucleotides and the like. For example, siRNAs, which are well known in the art, may include short nucleotide sequence (approximately 21-23 nucleotides), which have a base-paired structure characterized by two nucleotide 3'-overhangs (Tuschl and Borkhardt, Molecular Intervent. 2002, 2(3):158-67). The introduction of siRNAs into animal cells may result in the potent, long-lasting, specific post-transcriptional silencing of genes, for which the siRNA is directed against (Caplen et. al., Proc Natl Acad Sci U.S.A. 2001, 98:9742-7; Elbashir et. al., Nature. 2001, 411:494-8; Elbashir et al., Genes Dev. 2001, 15:188-200; Elbashir et. al., EMBO J. 2001, 20:6877-88). Methods and compositions for using siRNAs are described, for example, in U.S. Pat. No. 6,506,559. Methods of producing siRNA, 21-23 nucleotides in length from an in vitro system and use of the siRNA to interfere with mRNA of a gene in a cell or organism are described for example in WO0175164. The siRNA may also be made in vivo in a mammalian cell using a stable expression system. For example, a vector system, named pSUPER, that directs the synthesis of small interfering RNAs (siRNAs) in mammalian cells, was reported (Brummelkamp et. al., 2002, Science 296: 550-3). As detailed in Example 6 (and Table 5 therein), specific siRNA sequences, directed against the various CD44 variant transcripts, such as CD44V3, and/or CD44V6 and/or CD44V10 and/or CD44S may be prepared by any of the methods mentioned above herein. The siRNA may be administered by any methods known in the art, (such as described for example in Meade et. al., Adv Drug Deliv. Rev, 2007). The siRNA may be directed against various sequence regions of the mRNA of the various CD44 variant transcripts to ensure successful silencing of expression of the CD44V3, CD44V6, CD44V10, CD44S and any combination thereof. As detailed in Example 6, and shown in FIG. 7, expression levels of mRNA of various CD44 variants may be attenuated by use of specific siRNA molecules. As detailed in Example 6, three siRNA molecules were designed against each of CD44S, CD44V3, CD44V3 and CD44V10 variants. The siRNA molecules were introduced into cells and expression levels of mRNA, and protein of the CD44 were detected by RT-PCR. Reference is now made to FIG. 7, which shows the effect of various siRNA molecules on the mRNA expression of various CD44 transcripts. Panel I of FIG. 7 illustrates an agarose gel pictogram showing the expression levels of CD44V3 transcript under different experimental conditions ("-RT"—no Reverse Transcriptase in the reaction; "NT"— Non Transfected cells; "NR"—Non Relevant siRNA; CD44V3 siRNA #1-#3—siRNA molecules with the respective sequences listed in Table 6). As shown in FIG. 7, panel I, expression levels of CD44V3 in the presence of at least two of the siRNA's are significantly reduced, whereas expression levels of the mRNA of the control gene Actin, and that of CD44S, remain unaffected. Panel II of FIG. 7 illustrates an agarose gel pictogram showing the expression levels of CD44V6 transcript under different experimental conditions ("-RT"—no Reverse Transcriptase in the reaction; "NT"— Non Transfected cells; "NR"—Non Relevant siRNA; CD44V6 siRNA #1-#3—siRNA molecules with the respective sequences listed in Table 6). As shown in FIG. 7, panel II, expression levels of CD44V6 in the presence of at least two of the siRNA's are significantly reduced, whereas expression levels of the mRNA of the control gene Actin, and that of CD44S, remain unaffected. Panel III of FIG. 7 illustrates an agarose gel pictogram showing the expression levels of CD44V10 transcript under different experimental conditions ("-RT"—no Reverse Transcriptase in the reaction; "NT"— Non Transfected cells; "NR"—Non Relevant siRNA; CD44V10 siRNA #1-#3—siRNA molecules with the respective sequences listed in Table 6). As shown in FIG. 7, panel III, expression levels of CD44V10 in the presence of at least two of the siRNA's are significantly reduced, whereas expression levels of the mRNA of the control gene Actin, and that of CD44S, remain unaffected. Quantization analysis, presented in Table 7 of Example 6 show that siRNA molecules are able to significantly reduce the expression of the mRNA of the various CD44 variants.

Antisense technique is generally used to attenuate and/or inhibit the expression of a target (which may include DNA or RNA molecules, such as, for example, mRNA molecule) and may involve RNA-RNA interactions, RNA-DNA interactions, triple helix interactions, ribozymes and RNase-H mediated effect. Antisense nucleic acid molecules (such as antisense oligonucleotides) are usually a single stranded nucleic acid molecule which, upon hybridizing with complementary bases in an RNA or DNA molecule (the target), may attenuate and/or inhibit expression of the target that may include, for example, a specific gene, an mRNA molecule and the like. The antisense nucleic acid molecules may be prepared synthetically or encoded by a recombinant gene for expression in a cell. Some non-limiting examples of synthetic oligonucleotides may include oligonucleotides that contain phosphorothioates, phosphotriesters, methyl phosphonates, short chain alkyl, or cycloalkyl intersugar linkages or short chain heteroatomic or heterocyclic intersugar linkages. Nitrogen linkers or groups containing nitrogen can also be used to prepare oligonucleotide mimics. Also included are phosphoramidate and phosphorothioamidate oligomeric compounds, and oligonucleotides having morpholino backbone structures. A peptide-nucleic acid (PNA) backbone may also be used, in which the phosphodiester backbone of the oligonucleotide may be replaced with a polyamide backbone, the bases being bound directly or indirectly to the aza nitrogen atoms of the polyamide backbone. Other synthetic oligonucleotides may contain substituted sugar moieties comprising one of the following at the 2' position: OH, SH, $SCH_3$, F, OCN, $O(CH_2)_nH_2$ or $O(CH_2)_nH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_2$; $NH_2$; heterocycloalkyl; heterocycloalkaryl; aminoalkylamino; polyalkylamino; substituted silyl; a fluorescent moiety; an RNA cleaving group; a reporter group; an intercalator; a group for improving the pharmacokinetic and/or pharmacodynamic properties of an oligonucleotide; and other substituents having similar properties. Oligonucleotides may also have sugar mimetics such as cyclobutyls or other carbocyclics in place of the pentofuranosyl group. Antisense molecules, such as, for example, antisense oligonucleotides directed against the various CD44 variant transcripts, such as CD44V3, and/or CD44V6 and/or CD44V10 may be prepared. The Antisense oligonucleotides may be directed against various sequence regions of the mRNA of the various CD44 variant transcripts to ensure successful attenuation/silencing of expression of the CD44V3, CD44V6, CD44V10, and any combination thereof. The use of antisense oligonucleotides is performed under favorable cellular condition, which include optimal temperature and buffering conditions, such as, for example, as described in Du L. et al, PNAS, 2007, 104:6007-12; Hua et. al., PloS Biol. 2007, 5:e73).

According to some embodiments, oligonucleotides directed against various regions of the CD44 variant transcript sequences, such as CD44V3, CD44V6, CD44V7, CD44S and/or CD44V10, which are designed to attenuate (down-regulate) expression of these transcripts, may be used for treating neurodegenerative diseases. The oligonucleotides may include, for example, siRNA molecules, such as described hereinabove and in Example 6. Therefore, there is thus provided a method of treating of neurodegenerative diseases in a patient which may include administration of a composition comprising a reagent capable of attenuating expression of RNA encoded by a nucleic acid, wherein the nucleic acid is selected from a group consisting of: SEQ ID NO: 1, SEQ ID NO: 3, SEQ ID NO: 7, or any combination thereof. The reagent may include, for example, one or more polynucleotide, capable of hybridizing with said nucleic acid. The one or more polynucleotide may include DNA, RNA, siRNA, or any combination thereof. For example, the reagent may include one or more SMEs, such as, for example, an ERK MAP-kinase pathway modulator, a PKC modulator, and the like. For example, the method may include introducing antisense nucleic acid and/or siRNA molecule that targets the RNA (mRNA) of various CD44 variants, such as CD44V3, CD44V6, CD44V7, CD44S and/or CD44V10 into a patient, a patient cell, or organism with neurodegenerative disease; maintaining the cell or organism introduced with the oligonucleotide under conditions which favor the interaction of the oligonucleotides with the target mRNA of the various CD44 splice variants; and verifying the downregulation of expression of the various CD44 splice variants, CD44V3, CD44V6, CD44V7 CD44V10, CD44S, or any combination thereof and thereby treating the neurodegenerative disease.

According to some embodiments, small molecular entities (SME) may be identified that may affect (modulate) activity and/or expression of various CD44 splice variants. Small molecular entities may include any molecule or substance that may interact with the CD44 splice variants and disrupt the CD44 variant interaction with its physiologically relevant ligands. For example, SME may be developed in silico, using the appropriate hardware and software that are known in the art to identify substances. SME may be developed, for example, by in-vitro and vivo screening of chemical libraries, for molecular entities that are capable of interacting with the CD44 splice variants. For example, the binding of CD44 splice variants, such as CD44V3, CD44V6 and/or CD44V10 with the physiological ligand hyaloronic acid and its derivatives may be assessed in the presence or absence of the SME. Likewise, interaction of CD44V3, CD44V6 and/or CD44V10 may be tested in the presence or absence of suspected SME. The SMEs thus identified may be used to affect (modulate) the activity and/or expression of the various CD44 splice variants. For example, the SME may be used as antagonists of the CD44 splice variants. For example, the SME may be used as agonist of the CD44 splice variants. For example, the SME may include any molecule or substance that may directly or indirectly affect (modulate) the expression of the various CD44 variants. For example, the SME may include an inhibitor and/or an activator that may be used to directly or indirectly decrease (attenuate) and/or increase the expression level of various CD44 variants.

Figure 8:
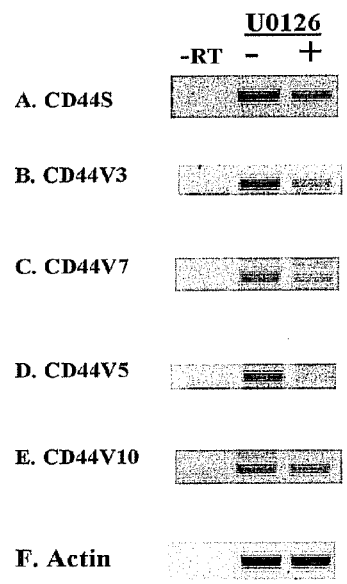
FIG. 8 demonstrates SME effect on mRNA expression of various CD44 variants, according to some embodiments.

For example, it has been shown that the ERK MAP-kinase pathway may be involved in the regulation of CD44 alternative splicing (Weg-Remers et. al., EMBO J. 2001, 20:4194-203). In accordance with some embodiments, the involvement of the ERK pathway on CD44 alternative splicing on cells of neuronal origin is detailed in Example 7 and shown in FIG. 8. Cell cultures of mouse NSC-34 cells, which are derived from fusion of embryonic spinal cord motor neurons and neuroblastoma cells were plated and either left untreated or treated with a MEK inhibitor U0126. Expression levels of mRNA of CD44 variants were detected by RT-PCR. As shown in FIG. 8, modulating (by inhibition) of the ERK-MAPK pathway by U0126 causes a significant reduction of CD44 variant exon splicing. As shown in FIG. 8, panel A, the mRNA levels of CD44S do not change in the presence of the inhibitor (U0126). As shown in FIG. 8, panel B, the mRNA levels of CD44V3 are reduced in the presence of the inhibitor ("+", right lane) as compared to the expression levels of CD44V3, in the absence of the inhibitor ("−", middle lane). As shown in FIG. 8, panel C, the mRNA levels of CD44V7 are reduced in the presence of the inhibitor ("+", right lane) as compared to the expression levels of CD44V7, in the absence of the inhibitor ("−", middle lane). As shown in FIG. 8, panel D, the mRNA levels of CD44V5 are reduced in the presence of the inhibitor ("+", right lane) as compared to the expression levels of CD44V5, in the absence of the inhibitor ("−", middle lane). As shown in FIG. 8, panel E, the mRNA levels of CD44V10 are reduced in the presence of the inhibitor ("+", right lane) as compared to the expression levels of CD44V10, in the absence of the inhibitor ("−", middle lane). Further shown in FIG. 8, panel F is a control, demonstrating lack of effect of the inhibitor U0126, on the expression of a control gene, Actin. Also, the left hand lane of panels A-F is a negative control performed in the absence of the RT enzyme ("−RT"). Thus, small molecules, which are known to modulate the ERK pathway, may further be used for modulation of CD44 alternative splicing in neuronal cells.

Reagents described hereinabove, which are designed to modulate (by down regulating (attenuating) and/or by increasing) expression and/or activity of the various CD44 splice variants aimed at the treatment of neurodegenerative disease of a patient, such as, for example, siRNA molecules, may be provided to the patient as is, or may be a part of a pharmaceutical composition where it is mixed with a pharmaceutically acceptable carrier and excipients. The siRNA molecules may be further introduced, for example, to a cell, a tissue, and the like, of the patient. The reagents and/or pharmaceutical compositions containing them may be provided by any known administration route. The reagents may also be presented in a pack or dispenser device, such as a kit. In addition, the reagents may also be administered in combination with various other active ingredients.

Reagents described hereinabove, which are designed to detect and quantitate expression of the various CD44 splice variants and the CD44 splice variants products, may be provided in the form of a kit. For example, the kit may include a kit for diagnosing a neurodegenerative disease. The kit may include at least one reagent capable of detecting the expression of a nucleic acid in a biological sample, wherein the nucleic acid may include SEQ ID NO: 1, SEQ ID NO:3, SEQ ID NO:5, SEQ ID NO:7, or any combination thereof. The reagent may include, for example, an oligonucleotide that is capable of hybridizing with the nucleic acid or with an RNA molecule encoded by the nucleic acid. For example, the kit may include at least one reagent capable of detecting the expression of a polypeptide in a biological sample, wherein the polypeptide may include SEQ ID NO: 2, SEQ ID NO:4, SEQ ID NO:6, SEQ ID NO:8, or any combination thereof. The reagent may include, for example, an antibody adapted to specifically interact with the polypeptide and to form detectable immuno-complexes with the polypeptide.

According to other embodiments, recombinant constructs, such as for example expression vectors, which may include the coding sequences of the various CD44 splice variants, such as CD44V3 coding sequence or CD44V6 coding sequence or CD44V7 coding sequence or CD44V10 coding sequence, may be prepared. The constructs may include a vector such a plasmid or viral vector, into which the nucleotide sequence of the CD44 splice variants is inserted in a forward or reverse orientation. In addition, the construct may further include regulatory sequences, such as a promoter. The constructs may further include additional coding sequences of various other non-related proteins and/or peptides that may be inserted in-frame before or after the CD44 splice variants nucleotide sequences. The nucleotide sequences of the CD44 splice variants introduced into the vector may include the entire, full length, coding sequence, or only a partial sequence of the CD44 splice variant transcript. Selection of the vectors and construction of the recombinant constructs may be performed by any of the methods known in the art. The recombinant constructs may be used, for example, to derive expression of the various CD44 splice variants, such as CD44V3, CD44V6, or CD44V7 and/or CD44V10 in various biological systems, for experimental, diagnostic and/or therapeutic purposes.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

EXAMPLES

Example 1

Expression of CD44V3, CD44V6 and CD44V10 in Hippocampi of AD Patients and Normal Control Total RNA was extracted from frozen hippocampi samples isolated from post mortem AD patients and normal controls (EZ RNA kit, Beit Haemek). RNA was then used in semi-quantitative RT-PCR analysis. First, RNA was subjected to the reverse transcription reaction (RT). Reverse transcription was performed with 5 U of SuperScript II reverse transcriptase (Invitrogen). The reaction mixes were incubated for 1 h at 42 degrees C. PCR steps were performed in a microprocessor-controlled incubator using 1 µl of the RT reactions in a reaction volume of 20 µl, containing 200 µM dNTPs, 1.25 U Thermoprime Plus DNA polymerase (ABgene) and 0.5 mM primers:

```
V3_F:
5'-TGACCACACAAAACAGAACCA-3'

C6_R:
5'-CCCATGTGAGTGTCCATCTG-3'

C5_F:
5'-GAGCAGCACTTCAGGAGGTTAC-3'

V6_R:
5'-GGGTAGCTGTTTCTTCCGTTG-3'

C5V10_F:
5'-GACAGAATCCCTGCTACCAATAGG-3'

V10C6_R:
5'-GGAATGTGTCTTGGTCTCCTGAT-3'
```

42 cycles were carried out for amplifications, each consisting of 1 min at 94 degrees C., 1 min at 55 degrees C. and 1 min at 72 degrees C. In addition, primers for Actin were included in the PCR reaction for normalization of the results. Amplification products were purified from agarose gel (QIAquick gel extraction kit, Qiagen) and sequenced using one of the primers used in the PCR reaction. Sequence data was analyzed using BlastN algorithm run on human RefSeq and genomic database (NCBI).

The results of the semi-quantitative RT-PCR are summarized in Table 1. The left column of Table 1 indicates the identity of the variant exons and the connection bridges to the constant exons as validated by sequencing. Level of expression of the various PCR products was determined by the relative band strength observed in the agarose gel. Level of relative expression is indicated by number of + signs (1, 2 and 3), which represent weak, moderate or strong expressions, respectively. 0 stands for no band observed (meaning no expression) and ND stands for unperformed reaction.

TABLE 1

| Variant exons | AD patients | | | | | Normal patients | | | | |
|---|---|---|---|---|---|---|---|---|---|---|
| Patient # | 1 | 2 | 3 | 4 | 5 | 11 | 12 | 13 | 14 | 15 |
| V2 | 0 | 0 | ++ | ++ | 0 | 0 | 0 | 0 | 0 | 0 |
| V2-V3 | 0 | 0 | 0 | ++ | ++ | 0 | 0 | 0 | 0 | 0 |
| V3-C6 | ++ | ++ | ++ | ++ | ++ | + | ++ |  | ++ | 0 |
| C5-V3 | ++ | ++ | ++ | ++ | ++ | 0 | 0 | 0 | + | + |
| C5-V4 | 0 | 0 | 0 | ++ | ++ | 0 | 0 | 0 | 0 | 0 |
| C5-V4-V5 | 0 | + | + | + | 0 | + | + | 0 | + | 0 |
| V6-V7 | + | 0 | 0 | ++ | 0 | 0 | 0 | 0 | 0 | 0 |
| V6-C6/C5-V6 | ++ | ++ | ++ | ++ | ++ | + | 0 | 0 | + | 0 |
| C5-V7 | 0 | 0 | 0 | ++ | 0 | 0 | 0 | 0 | 0 | 0 |
| V7-V8-C6 | 0 | 0 | 0 | ++ | + | 0 | 0 | +++ | 0 | 0 |
| V6-V7-V8 | 0 | 0 | 0 | ++ | 0 | 0 | 0 | 0 | 0 | 0 |
| C5-V6-V10-C6 | 0 | 0 | 0 | ++ | 0 | ++ | 0 | 0 | 0 | 0 |
| V8-C6 | ++ | 0 | 0 | ++ | 0 | 0 | 0 | ++ | + | 0 |
| V8-V9-C6 | 0 | 0 | 0 | + | 0 | 0 | 0 | 0 | ++ | 0 |
| V8-V9-V10-C6 | 0 | 0 | 0 | 0 | 0 | 0 | 0 | 0 | 0 | 0 |
| C5-V10-C6 | +++ | ++ | ++ | ++ | ++ | + | + | + | + | + |

Example 2

Expression of CD44S, CD44V3, CD44V6 and CD44V10 in Brains of AD Compared to Normal Controls by Real-Time PCR Total RNA is extracted from frozen hippocampal samples isolated from post mortem AD patients (n=10) and normal controls (n=10) using EZ RNA kit (Beit Haemek). Total RNA concentration is determined using the nanodrop 1000 machine (Thermo Scientific). 1.5 µg of RNA from each sample is reverse transcribed using Bioscript reverse transcriptase (Bioline), according to the manufacturer's instructions. The reaction mixes are incubated for 1 h at 42° C. Platinum SYBR Green qPCR SuperMix-UDG (Invitrogen)

reagent is used for qPCR along with 500 nM primers. Standard curve is performed (on six concentrations of cDNA pools in duplicates) for each pair of primers, to confirm linearity of the qPCR reaction and in order to transform the Ct experimental values to relative expression values. The real time PCR cycle program is as follows: 50° C., 2 min, 95° C., 2 min, then 40 cycles of 95° C. 15 sec and 60° C. 34 sec. All qPCR reactions are run on Applied Biosystems 7500 Real-Time PCR System (ABI).

The data indicate that significant increase in expression of CD44S, CD44V3, CD44V6, CD44V10 in AD patients compared to age and sex matched normal controls.

TABLE 2 relative expression of CD44S and CD44 variants as a ratio GAPDH in AD patients and normal controls

| Variant: | AD | Normal | AD/normal ratio | P value (t-test) |
|---|---|---|---|---|
| CD44S | 2.33 | 0.47 | 4.95 | 0.035 |
| V3 | 1.22 | 0.2 | 7.17 | 0.008 |
| V6 | 3.65 | 0.52 | 7.02 | 0.002 |
| V10 | 8.35 | 0.46 | 18.15 | 0.007 |

Example 3

Expression of CD44V7 in $APP_{751}$ Transgenic Mice and Normal Control

To characterize the expression of CD44V7 variant in AD-like pathology, hAPP mice that express human $APP_{751}$ containing the London (V717I) and Swedish (K670M/N671L) mutations (both mutations were found to be associated with familial AD) under the regulation of the murine Thy-1 promoter, are used. The $APP_{751}$ mice develop amyloid plaques in the neocortex and hippocampus at the age of 4-6 months and show memory deficit starting at 6 months. Hippocampal tissues are isolated from 7-7.5 months old female $APP_{751}$ transgenic mice and non-transgenic litter mates. RNA is extracted using EZ-RNA (Beit Haemek). Equal amounts of total RNA are reverse transcribed into cDNA using 5 U of SuperScript II reverse transcriptase (Invitrogen). The reaction mixes are incubated for 1 h at 42° C. Semi-quantitative PCRs step are preformed in a microprocessor-controlled incubator using 1 μl of the RT reaction volume of 20 μl, containing 200 μM dNTPs, 1.25 U Thermoprime plus DNA polymerase (Larova) and 0.5 μM oligonucleotide from the list below:

```
C3F:
5'-TCTGTGCAGCAAACAACACA

C6R:
5'-CCCATGTGAGTGTCCATCTG

V7F:
5'-TGTTTCCTGGACAGATTTCTTCG

Actin F:
5'-CTCCCTGGAGAAGAGCTACGAG

Actin R:
5'-CGTCATACTCCTGCTTGCTGAT
```

The step cycle program for the PCR includes denaturation at 94° C. for 30 seconds, annealing at 58° C. for 30 seconds and extension at 72° C. for 30 seconds for 42 cycles (for CD44V7), 32 cycles (for CD44S amplification) or 25 cycles (for β-Actin which is used as a reference gene). Band intensities of PCR products run on agarose gel are quantified using TotalLab software. A 7.2 fold increase is observed in the expression of mRNA containing a transcript having V7-C10 junction in $APP_{751}$ mice as compared to non-transgenic mice. A 16% increase in CD44S is observed under similar conditions.

Example 4

Expression of CD44V3, CD44V6 and CD44V10 in Lumbar Cord and Motor Cortex of ALS Patients and Normal Control Tissues were obtained from the Human Brain and Spinal Fluid Resource Centre (CA, USA). RNA is extracted from the lumbar cord and motor cortex of ALS patients as well as sex and age matching normal controls. The RNA is used in a semi-quantitative RT-PCR reaction as detailed in example 1. The results of the semi-quantitative RT-PCR performed on RNA samples obtained from motor cortex and lumbar cord of ALS patients and normal control is presented in Table 3. The left column of Table 3 indicates the identity of the variant exons and the connection bridges to the constant exons as validated by sequencing. Level of expression of the various PCR products was determined by the relative band strength observed in the agarose gel. Level of relative expression is indicated by number of + signs (1, 2 and 3), which represent weak, moderate or strong expressions, respectively. 0 stands for no band observed (meaning no expression observed) and ND stands for unperformed reaction.

TABLE 3

| Variant exons | ALS patients | | | | | Normal controls | | | |
|---|---|---|---|---|---|---|---|---|---|
| Patient # | 1 | 2 | 3 | 4 | 5 | 6 | 7 | 8 | 9 |
| Motor cortex | | | | | | | | | |
| CD44s | ++ | ++ | +++ | ++ | ++ | + | ++ | ++ | 0 |
| V3-C6 | 0 | + | 0 | 0 | 0 | 0 | 0 | + | 0 |
| V6-C6 | 0 | + | 0 | ++ | 0 | 0 | 0 | + | 0 |
| C5-V10 | 0 | 0 | 0 | 0 | 0 | 0 | 0 | 0 | 0 |
| C5-V10-C6 | 0 | 0 | +++ | ++ | ++ | 0 | 0 | + | 0 |
| Lumbar cord | | | | | | | | | |
| CD44s | ++ | +++ | +++ | +++ | +++ | ++ | +++ | +++ | +++ |
| C5-V3 | 0 | +++ | ++ | ++ | +++ | 0 | ++ | ++ | ++ |
| V3-C6 | + | +++ | +++ | +++ | +++ | 0 | 0 | +++ | + |
| C5-V3-C6 | 0 | + | ++ | ++ | + | 0 | 0 | + | + |
| V5-C6 | 0 | +++ | 0 | 0 | 0 | 0 | 0 | 0 | 0 |
| C5-V6 | 0 | ++ | +++ | +++ | +++ | 0 | 0 | 0 | +++ |
| V6-C6 | ++ | +++ | ++ | ++ | +++ | 0 | ++ | ++ | ++ |
| C5-V6-C6 | 0 | +++ | + | +++ | +++ | 0 | 0 | 0 | ++ |
| V7-V8-V9-V10 | 0 | 0 | ++ | ++ | +++ | 0 | 0 | 0 | 0 |
| V6-V7-V8-V9-V10 | 0 | 0 | + | ++ | ++ | 0 | 0 | 0 | 0 |
| C5-V10 | 0 | ++ | + | ++ | +++ | 0 | 0 | 0 | 0 |
| C5-V10-C6 | + | +++ | +++ | +++ | +++ | + | + | + | + |

Example 5

Immunocytochemical Analysis of CD44 Splice Variants in AD Patients' Brains

8 μm sections are prepared from formalin fixed, paraffin embedded hippocampal tissues (Netherland's brain bank). Primary antibodies used are against CD44 (HCAM, rat clone IM7, Santa Cruz), CD44V3 (mouse monoclonal vff-327, ABcam), CD44V6 (rabbit polyclonal, Chemicon) and CD44V10 (rabbit polyclonal, Chemicon). Secondary antibodies used are against the relevant species conjugated to HRP, polymer-enhanced (Envision®, Dako), substrate: DAB. Negative controls are isotype matched serum controls for the rabbit polyclonal antibodies in a non-immune rabbit serum at the same protein concentration as the primary antibody and for the mouse antibodies a multiple isotype control (Dako). For the rat antibody it was a matched isotype control at the same protein concentration as the primary antibody. Table 4 summarizes the immunohistochemistry staining results.

The immunohistochemistry staining reveals differential cellular and subcellular localizations. Whereas CD44s is found mainly in astrocytes and within senile plaques, CD44 variants staining is found in neurons in intracytoplasmic paranuclear regions.

TABLE 4

Cellular localization of CD44S and variant proteins

| Antigen | Areas Evaluated | Cellular Localization |
|---|---|---|
| CD44S | Hippocampal formation* | 1. Plaques, staining in paleocortex adjacent to hippocampus. Discrete zones with strongly immunoreactive fibers are present that resemble senile plaques. A few neuronal somata within plaques are stained, but rarely in other locations<br>2. White matter is diffusely stained with perivascular staining typical for astrocytes |
| CD44V3 | Hippocampal formation | 1. Neurons: Intra-cytoplasmic - overlaps region of lipofuscsin<br>2. Astrocytes, mostly white matter |
| CD44V6 | Hippocampal formation | 1. Neurons: Intra-cytoplasmic - overlaps region of lipofuscsin<br>2. White matter staining (astrocytic) |
| CD4410 | Hippocampal formation | Neurons: Intra-cytoplasmic - overlaps region of lipofuscsin |

*Includes Hippocampal formation and adjacent structures, such as subiculum and entorhinal cortex Example 6 siRNA Experiments—Knockdown of CD44 Expression in Human Cells

Various siRNA molecules directed against various CD44 variants were designed using well established parameters, and their sequences are listed in Table 5, below. HeLa cells (plated 15×10⁴ cells in 6-well plates on the previous day) are transfected with the various siRNAs (IDT), at the final concentration of 10 nM using Lipofectamine RNAi Max (Invitrogen) in accordance with the manufacturers instructions. As a negative control, cells are left untransfected (NT) or were transfected with a non-relevant siRNA (NR) labeled with TYE 563 at its 5' end, the sequence of which does not have any significant homology to any known human mRNA. Cells transfected with CD44V6 siRNA are serum starved for 24 h post transfection and serum renewal for additional 8 h (as described, for example, in Cheng et al., Genes Dev. (2006) 20:1715-20). As A positive control, for this variant, the siRNA sequence used by Cheng et al was used as a reference (siRNA #2).

Total RNA is isolated from the Hela cells 48 h post transfection using EZ-RNA (Beit Haemek) and equal amounts of total RNA are reverse transcribed into cDNA using 5 U of SuperScript II reverse transcriptase (Invitrogen). The reaction mixes are incubated for 1 h at 42° C. Semi-quantitative PCR step are preformed in a microprocessor-controlled incubator using 1 μl of the RT reaction volume of 20 μl, containing 200 μM dNTPs, 1.25 U Thermoprime plus DNA polymerase (Larova) and 0.5 μM oligonucleotide from the list below:

```
C3F:
5'-TCTGTGCAGCAAACAACACA

C6R:
5'-CCCATGTGAGTGTCCATCTG

V3R:
5'-AGCCTGCTGAGATGGTATTTGA

V6R:
5'-GGGTAGCTGTTTCTTCCGTTG

V10R:
5'-TCTTCCACCTGTGACATCATTC

Actin F:
5'-CTCCCTGGAGAAGAGCTACGAG

Actin R:
5'-CGTCATACTCCTGCTTGCTGAT
```

The step cycle program for the PCR is set for denaturation at 94° C. for 30 Sec, annealing at 58° C. for 30 Sec and extension at 72° C. for 30 Sec for 42 cycles (V3, V6 and V10 amplification), 32 cycles (CD44S amplification) or 25 cycles (for β-Actin, which is used as a reference gene). For further quantization of the data, bands intensities were quantified using TotalLab software. Results of the quantization are presented in Table 6, which shows the ratios between CD44 variants and β-Actin (control gene), normalized to non-transfected cells (NT).

A significant reduction (>80%) in the mRNA expression level of CD44S, CD44V3, CD44V6 and CD44V10 is observed as a result of co-expression of at least one novel siRNA directed against each of the CD44 isoforms.

TABLE 5 siRNA sequences (5' to 3' direction) directed against various CD44 variants. All nucleotides in the siRNA sequences are ribonucleotides except for nucleotides followed by the letter d, which are deoxyribonucleotides

| CD44 Variant | # | Sense | Antisense |
|---|---|---|---|
| CD44V3 | 1 | AGAUGAAAGAGACAGACACCUCAdGdT | ACUGAGGUGUCUGUCUCUUUCAUCUUC |
| | 2 | CUGGAUCAGGCAUUGAUGAUGAUdGdA | UCAUCAUCAUCAUGCCUGAUCCAGAA |
| | 3 | GCAUUGAUGAUGAUGAAGAUU | UCUUCAUCAUCAUCAAUGC |
| CD44V6 | 1 | ACAACGGAAGAAACAGCUACCCAGA | UCUGGGUAGCUGUUUCUUCCGUUGUAC |
| | 2 | GCAACUCCUAGUAGUACAAdTdT | UUGUACUACUAGGAGUUGCdTdT |
| | 3 | ACAGATGGCATGAGGGATAUU | UAUCCCUCAUGCCAUCUGUUU |
| CD44V10 | 1 | GCAGGACCUUCAUCCCAGUGACCdTdC | GAGGUCACUGGGAUGAAGGUCCUGCUU |
| | 2 | CUACUUUACUGGAAGGUUA | UAACCUUCCAGUAAAGUAGUU |
| | 3 | GUUGGAGAUUCCAACUCUAUU | UAGAGUUGGAAUCUCCAACAG |
| NR | | CUUCCUCUCUUUCUCUCCCUUGUdGdA | UCACAAGGGAGAGAAAGAGAGGAAGGA |

TABLE 6

Quantization analysis of siRNA effect on various CD44 variants

|  | NT | NR | #1 | #2 | #3 |
|---|---|---|---|---|---|
| CD44V3/Actin | 1 | 1 | 0.05 | 0.16 | 1.47 |
| CD44V6/Actin | 1 | 1.4 | 0 | 0 | 1.1 |
| CD44V10/Actin | 1 | 1.2 | 1.61 | 0 | 0 |

Example 7

Modulation of CD44 Alternative Splicing by an Inhibitor of ERK-MAP Kinase in Cells of Neuronal Origin To test the involvement of the ERK pathway on CD44 alternative splicing on cells of neuronal origin, mouse NSC-34 cells, which are derived from fusion of embryonic spinal cord motor neurons and neuroblastoma cells, are used. NSC-34 cell cultures (plated $15 \times 10^4$ cells in 6-well plates on the previous day) were either left untreated or treated with 10 µM of the MEK inhibitor U0126 (Sigma) for 6 hrs. Total RNA is isolated from the cells using EZ-RNA kit (Beit Haemek) and equal amounts of RNA are reverse transcribed into cDNA using 5 U of SuperScript II reverse transcriptase (Invirtogen). The reaction mixes are incubated for 1 h at 42° C. Semi-quantitative PCR steps are preformed in a microprocessor-controlled incubator using 1 µl of the RT reaction volume of 20 µl, containing 200 µM dNTPs, 1.25 U Thermoprime plus DNA polymerase (ABgene) and 0.5 µM primer, of the following:

```
C5F:
5'-GAGCACCCCAGAAAGCTACATT-3

C7R:
5'-CCAGAAGTTGTGGTCACTCCAC-3

V3R:
5'-ATCATCAATGCCTGATCCAGA-3

V5F:
5'-CCACAGCCTCCTTTCAATAACC-3

V7F:
5'-TGTTTCCTGGACAGATTTCTTCG-3

V10F:
5'-TCTGGGTATTGAAAGGTGTAGCC-3

ActinF:
5'-CTCCCTGGAGAAGAGCTACGAG-3

ActinR:
5'-CGTCATACTCCTGCTTGCTGAT-3
```

The step cycle program for the PCR is set for denaturation at 94° C. for 30 Sec, annealing at 58° C. for 30 Sec and extension at 72° C. for 30 Sec for 42 cycles (V3, V7, V5 and V10 amplification) or 32 cycles (CD44S amplification). Actin control PCR is preformed for normalization of the results. As can be seen in FIG. 8, panels, B-E, inhibition of the ERK pathway by U0126 (right lane, "="), led to a significant reduction of CD44 variant exon splicing.

REFERENCES

Miyake, et al, (1990) Hyaluronate can function as a cell adhesion molecule and CD44 participates in hyaluronate recognition. J. Exp Med, 172:69-75.

Aruffo, et al, (1990) CD44 is the principal cell surface receptor for hyaluronate Cell, 61:1303-13.

Peach, et al, (1993) Identification of hyaluronic acid binding sites in the extracellular domain of CD44. J. Cell Biol, 122:257-64.

Jalkanen, et al, (1992) Lymphocyte CD44 binds the COOH-terminal heparin-binding domain of fibronectin. J Cell Biol, 116: 817-25.

Fasssen, et al, (1992) A cell surface chondroitin sulfate proteoglycan, immunologically related to CD44, is involved in type I collagen-mediated melanoma cell motility and invasion. J Cell Biol, 116: 521-31.

Dimitroff, et al, (2000) A distinct glycoform of CD44 is an L-selectin ligand on human hematopoietic cells. PNAS, 97: 13841-6.

Dimitroff, et al, (2001) CD44 is a major E-selectin ligand on human hematopoietic progenitor cells J Cell Biol, 153: 1277-86.

Fujimoto, et al, (2001) CD44 binds a chondroitin sulfate proteoglycan, aggrecan. Int Immunol, 13: 359-66.

Tsukita, et al, (1994) ERM family members as molecular linkers between the cell surface glycoprotein CD44 and actin-based cytoskeletons J Cell Biol, 126: 391-401.

Screaton, et al, (1992) Genomic structure of DNA encoding the lymphocyte homing receptor CD44 reveals at least 12 alternatively spliced exons. PNAS, 89: 12160-4.

Tölg, et al, (1993) Splicing choice from ten variant exons establishes CD44 variability NAR, 21: 1225-9.

Screaton, et al, (1993) The identification of a new alternative exon with highly restricted tissue expression in transcripts encoding the mouse Pgp-1 (CD44) homing receptor. Comparison of all 10 variable exons between mouse, human, and rat. J Biol Chem, 268: 12235-8.

Gunthert, (1993) CD44: a multitude of isoforms with diverse functions. Curr. Top Microbiol Immunol, 184: 47-63.

Ni, et al, (2002) Expression of CD44 variants in colorectal carcinoma quantified by real-time reverse transcriptase-polymerase chain reaction. J. Lab. Clin. Med, 139: 59-65.

Bell, et al, (1998) Influence of intron length on alternative splicing of CD44. Mol Cell Biol, 18: 5930-41.

Gunthert, et al, (1991) A new variant of glycoprotein CD44 confers metastatic potential to rat carcinoma cells. Cell, 65: 13-24.

Heider, et al, (1993) A human homologue of the rat metastasis-associated variant of CD44 is expressed in colorectal carcinomas and adenomatous polyps. J Cell Biol, 120: 227-33.

Wielenga, et al, (1993) Expression of CD44 variant proteins in human colorectal cancer is related to tumor progression. Cancer Res, 53: 4754-6.

Naor, et al, (2002) CD44 in cancer. Crit Rev Clin Lab Sci, 39: 527-79.

Lesley, et al, (1995) Site-specific de-N-glycosylation of CD44 can activate hyaluronan binding, and CD44 activation states show distinct threshold densities for hyaluronan binding. J Exp Med, 182: 431-7.

Stamenkovic, et al, (1991) The hematopoietic and epithelial forms of CD44 are distinct polypeptides with different adhesion potentials for hyaluronate-bearing cells. Embo J 1991, 10: 343-8.

Van der Voort, et al, (1995) Binding of cell-surface expressed CD44 to hyaluronate is dependent on splicing and cell type. Biochem Biophys Res Commun, 214: 135-144.

Reber, et al, (1990) Retardation of metastatic tumor growth after immunization with metastasis-specific monoclonal antibodies. Int J Cancer, 46: 919-27.

Rothman, et al, (1991) Human T cell activation by OKT3 is inhibited by a monoclonal antibody to CD44. J Immunol, 147: 2493-9.

Ristamaki, et al, (1994) Serum CD44 in malignant lymphoma: an association with treatment response. Blood, 84: 238-43.

Haynes, et al, (1991) Measurement of an adhesion molecule as an indicator of inflammatory disease activity. Up-regulation of the receptor for hyaluronate (CD44) in rheumatoid arthritis. Arthritis Rheum, 1991, 34: 1434-43.

Haegel, et al, (1993) Activated mouse astrocytes and T cells express similar CD44 variants. Role of CD44 in astrocyte/T cell binding J Cell Biol., 122: 1067-77.

Laman, et al, (1998) Therapy with antibodies against CD40L (CD154) and CD44-variant isoforms reduces experimental autoimmune encephalomyelitis induced by a proteolipid protein peptide Mult Scler., 4: 147-53.

Garin, et al, (2007) CD44 variant DNA vaccination with virtual lymph node ameliorates experimental autoimmune encephalomyelitis through the induction of apoptosis. J Neurol Sci., 258: 17-26.

Matsuoka, et al, (2000) CD44 splice variant involvement in the chronic inflammatory disease of the spinal cord: HAM/TSP. J Neuroimmunol. 2000, 102: 1-7.

Boillee, et al, (2006) ALS: a disease of motor neurons and their nonneuronal neighbors Neuron, 39-59.

Pehar, et al, (2005) Complexity of astrocyte-motor neuron interactions in amyotrophic lateral sclerosisNeurodegener. Dis., 2: 139-46.

Di Giorgio, (2007) et al, Non-cell autonomous effect of glia on motor neurons in an embryonic stem cell-based ALS model Nat Neurosci., 10: 608-614.

Esposito, et al, (2007) Non-steroidal anti-inflammatory drugs in Parkinson's disease. Exp Neurol. 205: 295-312.

Kim, et al, (2006) Microglia, major player in the brain inflammation: their roles in the pathogenesis of Parkinson's disease. Exp Mol Med. 38: 333-47.

Haegel, et al, (1993) Activated mouse astrocytes and T cells express similar CD44 variants. Role of CD44 in astrocyte/T cell binding. J Cell Biol, 122: 1067-77.

Akiyama, et al, (1993) Morphological diversities of CD44 positive astrocytes in the cerebral cortex of normal subjects and patients with Alzheimer's disease. Brain Res., 632: 249-59.

Lobsiger, et. Al., (2007) Toxicity from different SOD1 mutants dysregulates the complement system and the neuronal regenerative response in ALS motor neurons. Proc Natl Acad Sci., 104(18):7319-26.

Guriec, et al, (1997) CD44 isoforms with exon v6 and metastasis of primary N0M0 breast carcinomas. Breast Cancer Res Treat., 44: 261-8

Merrifield J., (1964) Solid-phase peptide synthesis. 3. An improved synthesis of bradykinin. Biochemistry, 3:1385-90.

Ravikumar, et al, (004) Inhibition of mTOR induces autophagy and reduces toxicity of polyglutamine expansions in fly and mouse models of Huntington disease. Nat. Genet, 36: 585-95D.

Shibata, et al, (2006) Regulation of intracellular accumulation of mutant Huntingtin by Beclin 1. J. Biol. Chem., 281: 14474-85.

Yu et al, (2005) Macroautophagy—a novel Beta-amyloid peptide-generating pathway activated in Alzheimer's disease. J. Cell Biol., 171: 87-98.

Pickford, et al, (2008) The autophagy-related protein beclin 1 shows reduced expression in early Alzheimer disease and regulates amyloid beta accumulation in mice. J Clin Invest., 118: 2190-99.

Tuschl and Borkhardt, (2002) Small interfering RNAs: a revolutionary tool for the analysis of gene function and gene therapy. Molecular Intervent., 2: 158-67.

Caplen, et al, (2001) Specific inhibition of gene expression by small double-stranded RNAs in invertebrate and vertebrate systems. Proc Natl Acad Sci U.S.A., 98: 9742-7.

Elbashir, et al, (2001) Duplexes of 21-nucleotide RNAs mediate RNA interference in cultured mammalian cells. Nature, 411: 494-8.

Elbashir, et al, (2001) RNA interference is mediated by 21- and 22-nucleotide RNAs Genes Dev., 15: 188-200.

Elbashir, et al, (2001) Functional anatomy of siRNAs for mediating efficient RNAi in Drosophila melanogaster embryo lysate. EMBO J., 20: 6877-88.

Brummelkamp, et al, (2002) A system for stable expression of short interfering RNAs in mammalian cells. Science, 296: 550-3.

Meade and Dowdy, (2007) Exogenous siRNA delivery using peptide transduction domains/cell penetrating peptides. Adv Drug Deliv. Rev., 59:134-40.

Du, L, et al, (2007) Correction of prototypic ATM splicing mutations and aberrant ATM function with antisense morpholino oligonucleotides. Proc Natl Acad Sci U.S.A, 104: 6007-12.

Hua, et al, (2007) Enhancement of SMN2 exon 7 inclusion by antisense oligonucleotides targeting the exon. PloS Biol., 2007, 5: e73.

Weg-Remers, et al, (2001) Regulation of alternative pre-mRNA splicing by the ERK MAP-kinase pathway. EMBO J., 20: 4194-203.

Cheng, et al, (2006) A positive feedback loop couples Ras activation and CD44 alternative splicing. Genes Dev. 20:1715-20

What we claim is:

1. A method of treating or inhibiting a neurodegenerative disease selected from the group consisting of: Alzheimer's disease and ALS, the method comprising administering to a subject a composition comprising a reagent capable of reducing expression and/or activity of a polypeptide, wherein the sequence of said polypeptide is selected from the group consisting of a contiguous amino acid sequence being at least 90% homologous to at least 10 amino acid of: coordinates 214-274 of SEQ ID NO:2, coordinates 214-275 of SEQ ID NO:4, coordinates 214-276 of SEQ ID NO: 6, coordinates 214-300 of SEQ ID NO:8, or any combination thereof.

2. The method of claim 1, wherein said contiguous amino acid sequence being at least 90% homologous to at least 10 amino acid of: SEQ ID NO:2 comprises: a contiguous amino acid sequence being at least 90% homologous to amino acid coordinates 1-403 of SEQ ID NO:2, a contiguous amino acid sequence being at least 90% homologous to amino acid coordinates 214-274 of SEQ ID NO:2, a contiguous amino acid sequence being at least 90% homologous to amino acid coordinates 214-232 of SEQ ID NO:2, a contiguous amino acid sequence being at least 90% homologous to amino acid coordinates 256-274 of SEQ ID NO:2, or any combination thereof.

3. The method of claim 1, wherein said contiguous amino acid sequence being at least 90% homologous to at least 10 amino acid of SEQ ID NO:4 comprises: a contiguous amino acid sequence being at least 90% homologous to amino acid coordinates 1-404 of SEQ ID NO:4, a contiguous amino acid sequence being at least 90% homologous to amino acid coordinates 214-275 of SEQ ID NO:4, a contiguous amino acid sequence being at least 90% homologous to amino acid coordinates 214-232 of SEQ ID NO:4, a contiguous amino acid sequence being at least 90% homologous to amino acid coordinates 257-275 of SEQ ID NO:4, or any combination thereof.

4. The method of claim 1, wherein said contiguous amino acid sequence being at least 90% homologous to at least 10 amino acid of SEQ ID NO:6 comprises: a contiguous amino acid sequence being at least 90% homologous to amino acid coordinates 1-405 of SEQ ID NO:6, a contiguous amino acid sequence being at least 90% homologous to amino acid coordinates 214-276 of SEQ ID NO:6, a contiguous amino acid sequence being at least 90% homologous to amino acid coordinates 214-232 of SEQ ID NO:6, a contiguous amino acid sequence being at least 90% homologous to amino acid coordinates 258-276 of SEQ ID NO:6, or any combination thereof.

5. The method of claim 1, wherein said contiguous amino acid sequence being at least 90% homologous to at least 10 amino acid of SEQ ID NO:8 comprises: a contiguous amino acid sequence being at least 90% homologous to amino acid coordinates 214-232 of SEQ ID NO:8, a contiguous amino acid sequence being at least 90% homologous to amino acid coordinates 282-300 of SEQ ID NO:8, or any combination thereof.

6. The method of claim 1, wherein said administering to a subject comprises administering to a patient, a cell of a patient, a tissue of a patient, or any combination thereof.

7. The method of claim 1, wherein said reagent comprises an antibody adapted to specifically bind said polypeptide.

8. The method of claim 7, wherein said antibody comprises a monoclonal antibody, a polyclonal antibody, or any combination thereof.

9. An isolated polynucleotide molecule comprising the sequence set forth in SEQ ID NO:3.

10. The complement of the polynucleotide molecule of claim 9, wherein the complement of the polynucleotide molecule and the polynucleotide molecule are 100% complementary.

11. A first polynucleotide derived from the isolated polynucleotide molecule of claim 9, wherein said first polynucleotide comprises a contiguous first nucleotide sequence being at least 90% homologous to nucleotide coordinates 639-825 of SEQ ID NO:3.

12. A second polynucleotide derived from the isolated polynucleotide molecule of claim 9, wherein said second polynucleotide comprises a contiguous second nucleotide sequence being at least 90% homologous to nucleotide coordinates 639-696 of SEQ ID NO:3.

13. A third polynucleotide derived from the isolated polynucleotide molecule of claim 9, wherein said third polynucleotide comprises a contiguous third nucleotide sequence being at least 90% homologous to nucleotide coordinates 769-825 of SEQ ID NO:3.

14. The isolated polynucleotide molecule of claim 9, wherein said polynucleotide molecule encodes a polypeptide comprising the sequence set forth in SEQ ID NO:4.

15. A first peptide derived from the polypeptide of claim 14, wherein said first peptide comprises a contiguous first amino acid sequence being at least 90% homologous to amino acid coordinates 214-275 of SEQ ID NO:4.

16. A second peptide derived from the polypeptide of claim 14, wherein said second peptide comprises a contiguous second amino acid sequence being at least 90% homologous to amino acid coordinates 214-232 of SEQ ID NO:4.

17. A third peptide derived from the polypeptide of claim 14, wherein said third peptide comprises a contiguous third amino acid sequence being at least 90% homologous to amino acid coordinates 257-275 of SEQ ID NO:4.

* * * * *